US011487136B2

(12) United States Patent
Johns et al.

(10) Patent No.: US 11,487,136 B2
(45) Date of Patent: Nov. 1, 2022

(54) CUSTOMIZED WAVEFRONT-GUIDED METHODS, SYSTEMS, AND DEVICES TO CORRECT HIGHER-ORDER ABERRATION

(71) Applicants:Boston Foundation for Sight, Needham, MA (US); University of Rochester, Rochester, NY (US)

(72) Inventors: Lynette Johns, East Walpole, MA (US); Geunyoung Yoon, Pittsford, NY (US); Olga Tomashevskaya, Watertown, MA (US); Deborah S. Jacobs, Brookline, MA (US)

(73) Assignees: Boston Foundation for Sight, Needham, MA (US); University of Rochester, Rochester, NY (US)

( * ) Notice: Subject to any disclaimer, the term of this patent is extended or adjusted under 35 U.S.C. 154(b) by 0 days.

(21) Appl. No.: 15/384,871

(22) Filed: Dec. 20, 2016

(65) Prior Publication Data

US 2017/0102557 A1    Apr. 13, 2017

Related U.S. Application Data

(62) Division of application No. 13/889,187, filed on May 7, 2013, now Pat. No. 9,554,889.
(Continued)

(51) Int. Cl.
*G02C 7/04* (2006.01)
*B29D 11/00* (2006.01)
(Continued)

(52) U.S. Cl.
CPC ............... *G02C 7/047* (2013.01); *A61F 2/14* (2013.01); *B24B 13/0025* (2013.01);
(Continued)

(58) Field of Classification Search
CPC . A61B 3/0025; A61B 3/1015; A61B 2576/02; B29D 11/00105;
(Continued)

(56) References Cited

U.S. PATENT DOCUMENTS 5,963,299 A * 10/1999 Reyburn ............... G02C 7/021
                                                33/507
6,199,986 B1    3/2001 Williams et al.
(Continued)

FOREIGN PATENT DOCUMENTS

CA         2776967 A1 *  4/2011  ............. G02C 7/061
WO    WO-2007/050453 A1   5/2007
WO    WO-2009/097409 A1   8/2009

OTHER PUBLICATIONS

International Search Report and Written Opinion for International Application No. PCT/US13/39993 dated Aug. 13, 2013. 18 pages.

*Primary Examiner* — Paul B Prebilic
(74) *Attorney, Agent, or Firm* — Wilmer Cutler Pickering Hale and Dorr LLP

(57) ABSTRACT

Methods and systems for manufacturing a wavefront-guided scleral lens prosthetic device customized for an eye of a patient include obtaining a first scleral lens prosthetic device with a central optic zone configured to vault over the eye's cornea and a peripheral haptic zone configured to align with the eye's sclera, collecting measurements of any offset and/or rotation of the first scleral lens prosthetic device relative to the eye's pupil and of any aberrations, particularly higher-order aberrations, generating a wavefront-guided profile from the measurements, and fabricating a second scleral lens prosthetic device with the profile on a surface of a central optic zone configured to vault over the eye's cornea and a peripheral haptic zone customized to align with the eye's sclera.

7 Claims, 14 Drawing Sheets

Related U.S. Application Data

(60) Provisional application No. 61/643,749, filed on May 7, 2012.

(51) Int. Cl.
*A61F 2/14* (2006.01)
*G02C 7/02* (2006.01)
*B24B 13/00* (2006.01)

(52) U.S. Cl.
CPC .. *B29D 11/00105* (2013.01); *B29D 11/00961* (2013.01); *G02C 7/021* (2013.01); *G02C 7/027* (2013.01); *G02C 7/04* (2013.01); *A61F 2240/002* (2013.01); *G02C 2202/22* (2013.01)

(58) Field of Classification Search
CPC .. B29D 11/00961; G02C 7/028; G02C 7/027; G02C 7/047; G02C 2202/22
See application file for complete search history.

(56) References Cited

U.S. PATENT DOCUMENTS

| | | | |
|---|---|---|---|
| 6,264,328 B1 | 7/2001 | Williams et al. | |
| 6,299,311 B1 | 10/2001 | Williams et al. | |
| 6,305,802 B1 | 10/2001 | Roffman et al. | |
| 6,338,559 B1 | 1/2002 | Williams et al. | |
| 6,491,394 B1* | 12/2002 | Blum | A61B 3/0025 351/228 |
| 6,499,843 B1 | 12/2002 | Cox et al. | |
| 6,827,444 B2* | 12/2004 | Williams | A61B 3/1015 351/212 |
| 6,988,801 B2 | 1/2006 | Yoon | |
| 7,036,931 B2 | 5/2006 | Lindacher et al. | |
| 7,044,603 B2 | 5/2006 | Yoon | |
| 7,296,890 B2 | 11/2007 | Svochak et al. | |
| 7,414,712 B2 | 8/2008 | Yoon | |
| 7,802,884 B2 | 9/2010 | Feldon et al. | |
| 7,815,310 B2 | 10/2010 | Su et al. | |
| 7,862,176 B2 | 1/2011 | Gemoules et al. | |
| 8,632,188 B1* | 1/2014 | Gemoules | A61B 3/125 351/212 |
| 8,985,767 B2* | 3/2015 | Spratt | G02C 7/027 351/159.74 |
| 9,658,470 B2 | 5/2017 | Applegate et al. | |
| 2002/0196412 A1* | 12/2002 | Abitbol | G02C 7/02 351/246 |
| 2003/0076478 A1* | 4/2003 | Cox | A61B 3/1015 351/219 |
| 2003/0090623 A1 | 5/2003 | Rubinstein et al. | |
| 2003/0107704 A1* | 6/2003 | Senda | G02C 7/061 351/159.42 |
| 2004/0057014 A1* | 3/2004 | Altmann | A61B 3/1015 351/246 |
| 2004/0156014 A1 | 8/2004 | Piers et al. | |
| 2004/0227932 A1 | 11/2004 | Yoon | |
| 2006/0173541 A1 | 8/2006 | Friel | |
| 2012/0062844 A1 | 3/2012 | Svochak et al. | |
| 2012/0274887 A1 | 11/2012 | Hwang et al. | |
| 2012/0274897 A1 | 11/2012 | Narasimha-Iyer et al. | |

* cited by examiner

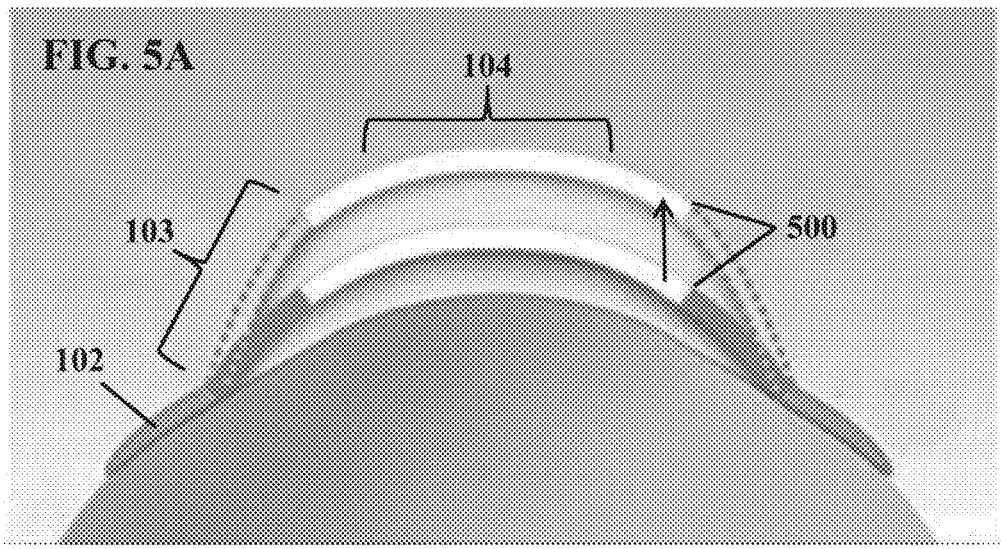
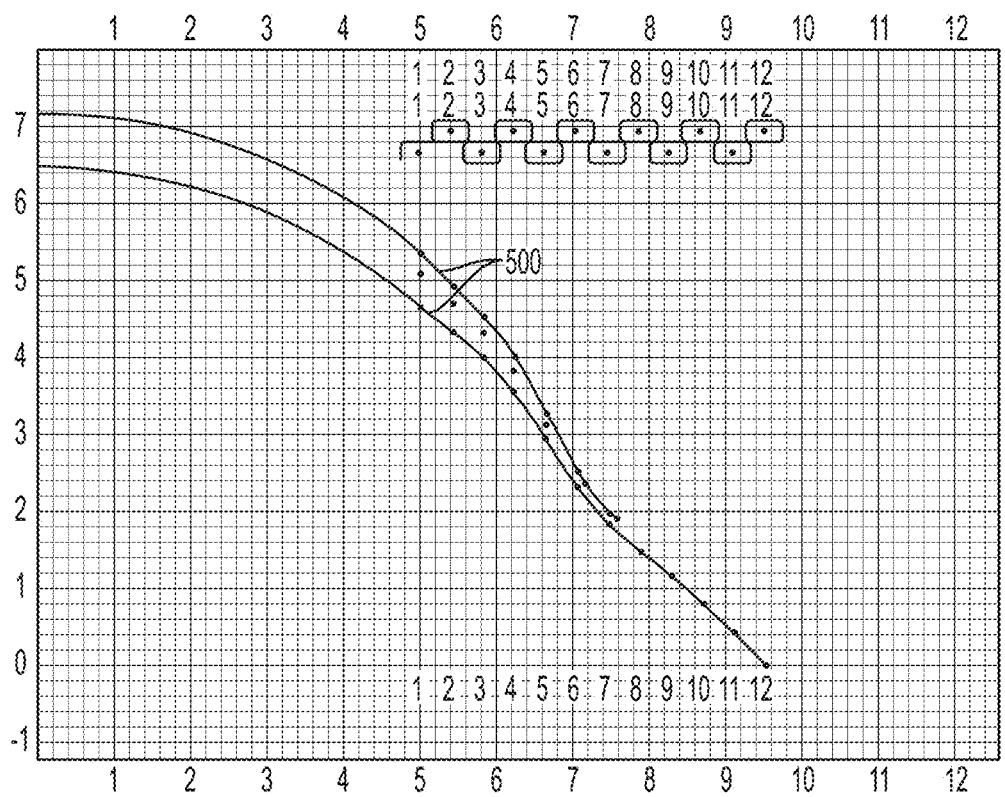
FIG. 5B

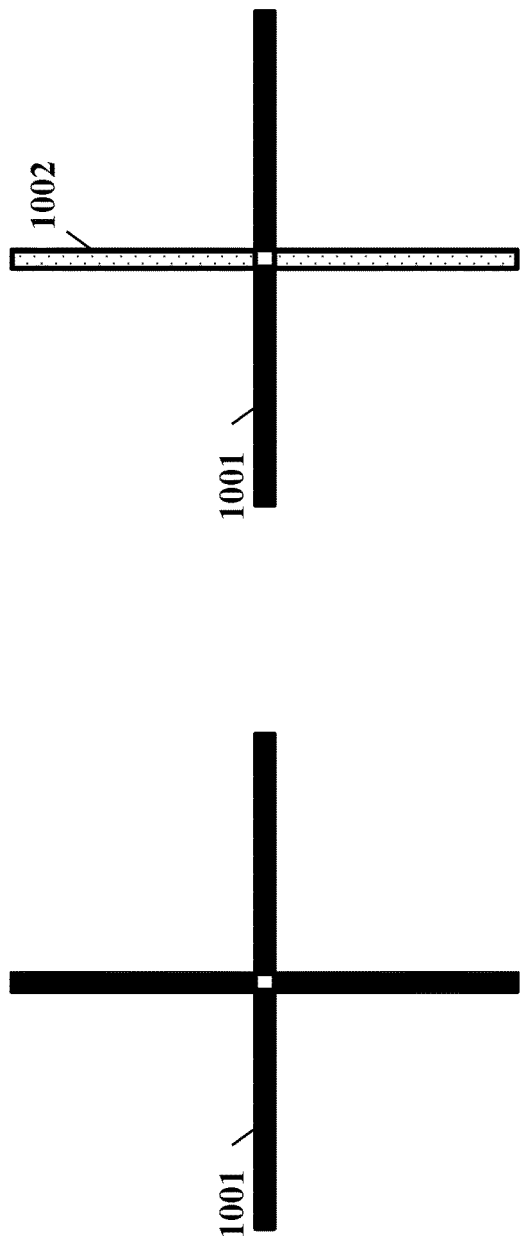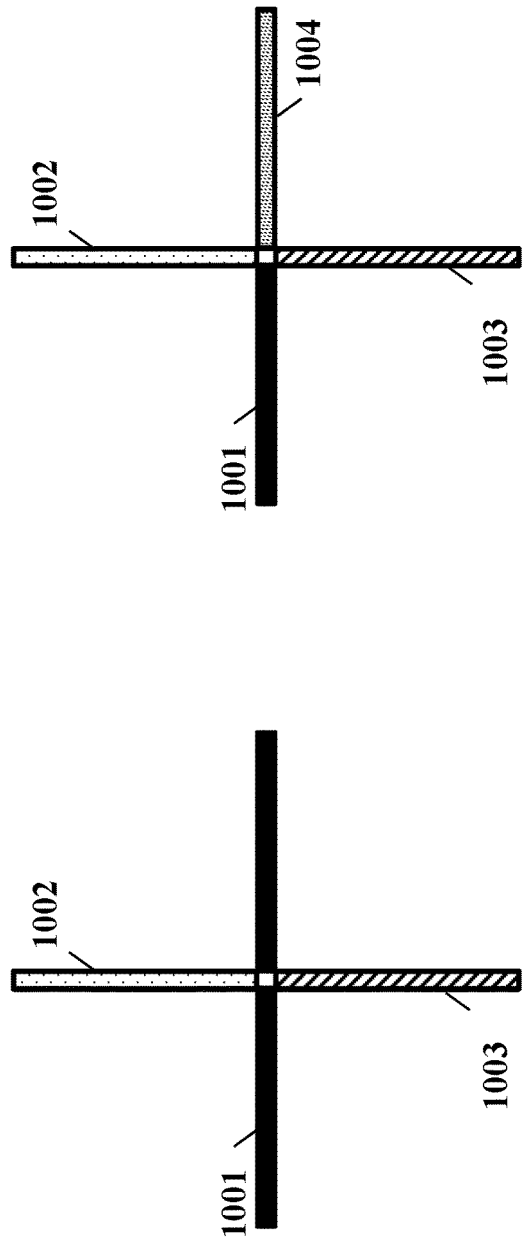

FIG. 18A          FIG. 18B
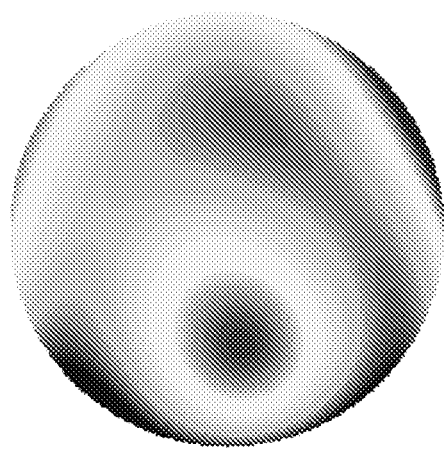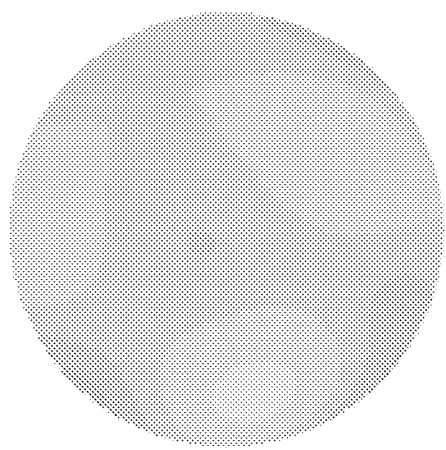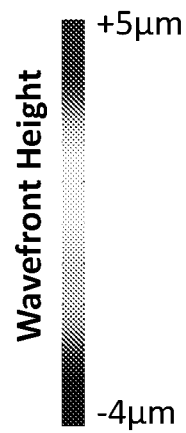
FIG. 19
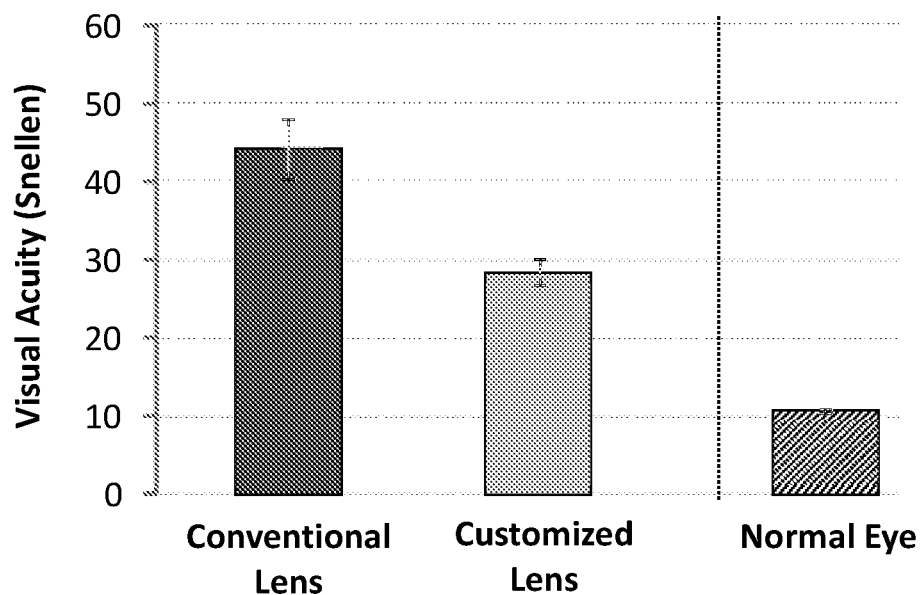

CUSTOMIZED WAVEFRONT-GUIDED METHODS, SYSTEMS, AND DEVICES TO CORRECT HIGHER-ORDER ABERRATION

RELATED APPLICATIONS

This application is a divisional application of U.S. patent application Ser. No. 13/889,187, filed on May 7, 2013, which issued on Jan. 31, 2017 as U.S. Pat. No. 9,554,889, which claims priority to and incorporates by reference the entire contents of provisional application No. 61/643,749, filed on May 7, 2012.

TECHNICAL FIELD

The present disclosure relates generally to ophthalmological and optometrical methods, systems, and devices. More specifically, the present disclosure relates to methods, systems, and devices for improving or at least maintaining vision and/or treating or at least reducing symptoms associated with ocular aberrations.

BACKGROUND

An eye is one of the most complex organs in the human body. The sclera of the eye is the white surface visible around the cornea. The iris is the pigmented part of the eye surrounding the aperture that is the pupil and adjusting the pupil size to control the amount of light entering the eye. The cornea, which allows light to enter and focuses the light as it enters the eye, is the clear front surface of the eye covering the iris and the pupil. The crystalline lens is behind the pupil and further focuses light. Light that reaches the retina, which is an optical sensory membrane in the back of the eyeball, is converted into electronic signals, which in turn are transmitted via optic nerve to the visual cortex in the brain to be interpreted as sight.

Due to its complexity and sensitivity, each individual eye is prone to a host of injuries and disorders. Ocular higher-order aberrations in the cornea, for example, may originate from a corneal dystrophy (i.e., a hereditary disorder), inflammation in the eye, surface abrasions, burns, and other trauma. Corneal ectasia is an umbrella term for a group of conditions that cause a progressive thinning and distortion of the corneal shape, including keratoconus, keratoglobus, pellucid, marginal degeneration, Terrien's marginal degeneration, post-LASIK (laser-assisted in situ keratomileusis) treatment, post-radial keratotomy, post-penetrating keratoplasty, and post-cornea transplantation or grafting.

While lower-order aberrations include common aberrations like defocus (e.g., nearsightedness and farsightedness) and regular astigmatism, higher-order aberrations may include secondary astigmatism, spherical aberration, coma, trefoil, and quadrafoil stemming from irregular deformations, stress lines, and scarring on the corneal surface. For example, keratoconus may change the corneal side profile from a normal gradual curve to a steeper curve to a pronounced conical shape. These structural irregularities may refract, reflect, and/or absorb light when it reaches the cornea, thus distorting (by causing, e.g., blurriness, ghosts, halos, starbursts, and loss of contrast) and sometimes multiplying the image received by the retina (diplopia or polyopia). Vision in low light or at night may be even more difficult because the pupil dilates to expose and receive light through even more of the irregular corneal surface. Other symptoms associated with ocular higher-order aberrations include eye strain, itching, pain, and photophobia (i.e., sensitivity to bright light). Patients with ocular higher-order aberrations may experience temporary or permanent visual distortions, and for some, their vision may progressively deteriorate.

In particular, the abnormal degenerative disorder of keratoconus, in which the cornea both steepens and thins, produces a large magnitude of higher-order aberrations, around 5-6 times typically found in normal eyes, thus severely degrading retinal image quality. For a 5.7 mm pupil, Guirao et al. theoretically demonstrated that an improvement by a factor of 12 in retinal image contrast at 16 cycles per degree (c/deg) could be achievable in an eye with keratoconus compared to only a 2.5-fold benefit in a normal eye. Similarly for a 6 mm pupil, when computing the area under the modulation transfer function, Pantanelli et al. estimated a 4.4-fold improvement in retinal image quality in an eye with keratoconus compared to only a 2.1-fold benefit in a normal eye. Therefore, an eye with keratoconus stands to benefit to a great extent by correcting higher-order aberrations.

In 1961, Smirnov theorized that upon quantifying the ocular higher-order aberrations of an eye it was conceivable to make ophthalmic lenses to neutralize the aberrations; however, he also conceded that this was highly impractical given the laborious nature of the aberration measurements.

Existing attempts to correct ocular higher-order aberrations and to treat underlying causes like corneal ectasia include soft contact lenses, hybrid contact lenses, rigid gas-permeable contact lenses, and conventional scleral lenses. However, these existing lenses help only a small percentage of patients and only to a limited extent. For example, both Sabesan et al. and Marsack et al. attempted to correct higher-order aberrations with soft contact lenses by incorporating centration information and accounting for the effect of the interaction of the ophthalmic lens with the ocular surface. Even then, the residual higher-order wavefront error was still $0.93 \pm 0.19$ μm for a 6 mm pupil in the Sabesan study. Similarly, the residual higher-order wavefront error was 0.31 μm and 0.38 μm for a 4.25 mm pupil in two keratoconus patients and 0.76 μm for a 4.5 mm pupil in a third keratoconus patient in the Marsack study.

Moreover, some patients have corneal scarring, recurrent corneal erosions due to poor-fitting contact lenses, and/or an intolerance to contact lenses. Although conventional scleral lenses minimize contact with the cornea by having a large diameter and a vaulted structure over the cornea, even these lenses only correct for lower-order aberrations and some higher-order aberrations but not residual higher-order aberrations originating from the posterior corneal surface, the crystalline lens (which may develop an aberration to compensate for a corneal aberration), and/or the scleral lens itself if the lens is decentered (e.g., due to a lack of individual patient customization).

When lenses fail to correct ocular higher-order aberrations and/or to treat other associated symptoms, clinicians may resort to more invasive procedures like corneal transplantation surgery, whereby a damaged or diseased cornea is replaced by donated corneal tissue. Together, keratoconus and post-refractive corneal ectasia are the second most frequent indication for corneal transplantation, accounting for about 15% of the corneal transplantations performed in the United States. In addition to common dangers associated with ocular surgery like infection, inflammation, injury, visual impairment, and temporary or permanent blindness, corneal transplantation carries both short-term and lifelong risks of corneal graft failure and rejection.

SUMMARY

An important feature of ocular higher-order aberrations in general is the inter-individual variability. Even though vertical coma and secondary astigmatism show a consistent trend (i.e., being negative in sign) across the keratoconus population, substantial variability exists in sign and magnitude of ocular higher-order aberrations. Therefore, a need remains for methods and systems that use each individual patient's optical profile to customize corrections for ocular higher-order aberrations.

Thus, patients and clinicians would benefit from new methods, systems, and devices for improving or at least maintaining vision and/or treating or at least reducing symptoms associated with higher-order aberrations. Ideally, these methods, systems, and devices would be patient-customized and help clinicians increase success rates for correcting ocular higher-order aberrations without resorting to more invasive and dangerous treatment options.

The methods, systems, and devices described here include recognizing and quantifying key factors for improving or at least maintaining vision and/or treating or at least reducing symptoms associated with ocular aberrations, particularly for translating the theoretical visual benefits of correcting higher-order aberrations into practical improvement in optical and visual performance. These methods and systems are directed to defining successful strategies, procedures, and clinical outcomes that are tailored for each patient with ocular higher-order aberrations.

In one embodiment, a method for manufacturing a wavefront-guided scleral lens prosthetic device customized for an eye of a patient includes obtaining a first scleral lens prosthetic device, having a central optic zone configured to vault over the eye's cornea and a peripheral haptic zone configured to align with the eye's sclera, collecting a first set of one or more measurements of any offset and/or rotation of the first scleral lens prosthetic device relative to the eye's pupil, collecting a second set of one or more measurements of one or more of any aberrations of the eye, and generating a wavefront-guided profile from the first and second sets of one or more measurements, the profile to be fabricated on a surface of a second scleral lens prosthetic device, having a central optic zone configured to vault over the eye's cornea and a peripheral haptic zone customized to align with the eye's sclera. The method further includes marking alignment points on the first scleral lens prosthetic device to collect the first set of one or more measurements of any offset and/or rotation of the first scleral lens prosthetic device relative to the eye's pupil.

In an embodiment, the one or more aberrations include a secondary astigmatism, a spherical aberration, a coma, a trefoil, a quadrafoil, and/or a different higher-order aberration caused by an irregular deformation, a stress line, and/or a scar on the eye's cornea.

In an embodiment, the method further includes fabricating the second scleral lens prosthetic device with said wavefront-guided profile on a surface of the second scleral lens prosthetic device. In an embodiment, fabricating the second scleral lens prosthetic device includes manufacturing the second scleral lens prosthetic device on a lathe.

In an embodiment, the method further includes determining a level of performance of the second scleral lens prosthetic device, and comparing the level of performance to one or more performance criteria indicative of the level to which a scleral lens prosthetic device limits fabrication error, performs optically, and/or performs visually. In an embodiment, the one or more performance criteria include optical metrology, visual acuity, and/or contrast sensitivity.

In an embodiment, the method further includes obtaining successive scleral lens prosthetic devices if the one or more performance criteria are not met by one or more previous scleral lens prosthetic devices, and repeating the steps of (a) collecting a first set of one or more additional measurements of at least one of any offset and rotation of a new first scleral lens prosthetic device relative to the eye's pupil when the new first scleral lens prosthetic device is worn on the eye, (b) collecting a second set of one or more additional measurements of one or more of any aberrations of the eye, (c) generating a new wavefront-guided profile using at least one of the first and second sets of one or more additional measurements, and/or (d) fabricating a new scleral lens prosthetic device with the new wavefront-guided profile on a surface of the new scleral lens prosthetic device, and determining a level of performance of each successive new scleral lens prosthetic device until the one or more performance criteria are met.

In one embodiment, a system for use with a first scleral lens prosthetic device, having a central optic zone configured to vault over the eye's cornea and a peripheral haptic zone configured to align with the eye's sclera, the system for manufacturing a wavefront-guided scleral lens prosthetic device customized for an eye of a patient includes a data collection unit for receiving (a) a first set of one or more measurements of any offset and/or rotation of the first scleral lens prosthetic device relative to the eye's pupil when the first scleral lens prosthetic device is worn on the eye, and (b) a second set of one or more measurements from a wavefront sensor of one or more of any aberrations of the eye, a processor to generate a wavefront-guided profile from the first and second sets of one or more measurements, said profile to be fabricated on a surface of a second scleral lens prosthetic device, having a central optic zone configured to vault over the eye's cornea and a peripheral haptic zone customized to align with the eye's sclera, and storage for storing data and executable instructions to be used by the processor.

In an embodiment, the one or more aberrations include a secondary astigmatism, a spherical aberration, a coma, a trefoil, a quadrafoil, and/or a different higher-order aberration caused by an irregular deformation, a stress line, and/or a scar on the eye's cornea. In an embodiment, the data collection unit is further configured to detect alignment points on the first scleral lens prosthetic device to collect the first set of one or more measurements. In an embodiment, the system further includes a fabrication unit to fabricate the second scleral lens prosthetic device with the wavefront-guided profile on a surface of the second scleral lens prosthetic device. In an embodiment, the fabrication unit includes a computer-controlled lathe configured to manufacture a scleral lens prosthetic device.

In an embodiment, the processor is further configured to determine a level of performance of the second scleral lens prosthetic device as compared to one or more performance criteria indicative of the level to which a scleral lens prosthetic device limits fabrication error, performs optically, and/or performs visually. In an embodiment, the one or more performance criteria include optical metrology, visual acuity, and/or contrast sensitivity.

In an embodiment, the processor is further configured, if the one or more performance criteria are not met by one or more previous scleral lens prosthetic devices, to repeat the steps of receiving (a) a first set of one or more additional measurements of any offset and/or rotation of the first scleral lens prosthetic device relative to the eye's pupil when the first scleral lens prosthetic device is worn on the eye, and (b) a second set of one or more additional measurements from a wavefront sensor of one or more of any aberrations of the eye, generating a new wavefront-guided profile using the first and/or second sets of one or more additional measurements, and/or fabricating a new scleral lens prosthetic device with the new wavefront-guided profile on a surface of the new scleral lens prosthetic device, and to determine a level of performance of each successive new scleral lens prosthetic device until the one or more performance criteria are met.

In one embodiment, a wavefront-guided scleral lens prosthetic device customized for an eye of a patient includes a peripheral haptic zone configured to align with the eye's sclera and a central optic zone configured to vault over the eye's cornea, having a wavefront-guided surface profile generated from a first set of one or more measurements of any offset and/or rotation of the scleral lens prosthetic device relative to the eye's pupil and a second set of one or more measurements of one or more of any aberrations of the eye. In an embodiment, the one or more of any aberrations include a secondary astigmatism, a spherical aberration, a coma, a trefoil, a quadrafoil, and/or a different higher-order aberration caused by an irregular deformation, a stress line, and/or a scar on the eye's cornea.

In one embodiment, a method for manufacturing a wavefront-guided scleral lens prosthetic device customized for an eye of a patient includes predicting a first set of one or more measurements of any offset and/or rotation relative to the eye's pupil representative of an interaction between a scleral lens prosthetic device and the eye, receiving a second set of one or more measurements of one or more of any aberrations of the eye, generating a wavefront-guided profile from the first and second sets of one or more measurements, and fabricating a scleral lens prosthetic device, having a central optic zone configured to vault over the eye's cornea and a peripheral haptic zone customized to align with the eye's sclera, with the wavefront-guided profile on a surface of the scleral lens prosthetic device.

In an embodiment, a non-transitory media for storing instructions that, when executed, include, responsive to a first set of one or more measurements of any offset and/or rotation of a scleral lens prosthetic device relative to the eye's pupil, and responsive to a second set of one or more measurements from a wavefront sensor of one or more of any aberrations of the eye, generating a wavefront-guided profile from the first and second sets of one or more measurements, and determining instructions to cause a fabrication unit to fabricate a scleral lens prosthetic device, having a central optic zone configured to vault over the eye's cornea and a peripheral haptic zone customized to align with the eye's sclera, with said wavefront-guided profile on a surface of the scleral lens prosthetic device.

The details of one or more embodiments of the present inventions are set forth in the accompanying drawings and the description below. Other features, objects, and advantages will be apparent from the description and drawings, and from the claims.

BRIEF DESCRIPTION OF THE DRAWINGS

FIG. 5A is a schematic diagram of a scleral lens prosthetic device illustrating how a transitional zone is used to allow for vault independent of base curve according to some embodiments of the present inventions;

FIG. 5B is a display screen shot of a platform used for customization of scleral lens prosthetic devices according to some embodiments of the present inventions;

FIGS. 10A-10D are diagrammatic representations of various radially symmetric and asymmetric haptic types according to some embodiments of the present inventions;

FIGS. 18A-18B are wavefront maps of an eye with advanced keratoconus measured with a conventional scleral lens and with a customized scleral lens prosthetic device, using a Shack-Hartmann wavefront sensor according to some embodiments of the present inventions; and FIG. 19 is a plot of the visual acuity, measured with a conventional scleral lens and with a customized scleral lens prosthetic device in an eye with advanced keratoconus, and the average visual acuity, measured in four normal eyes with comparable native optical quality, according to some embodiments of the present inventions.

DETAILED DESCRIPTION

Figure 2:
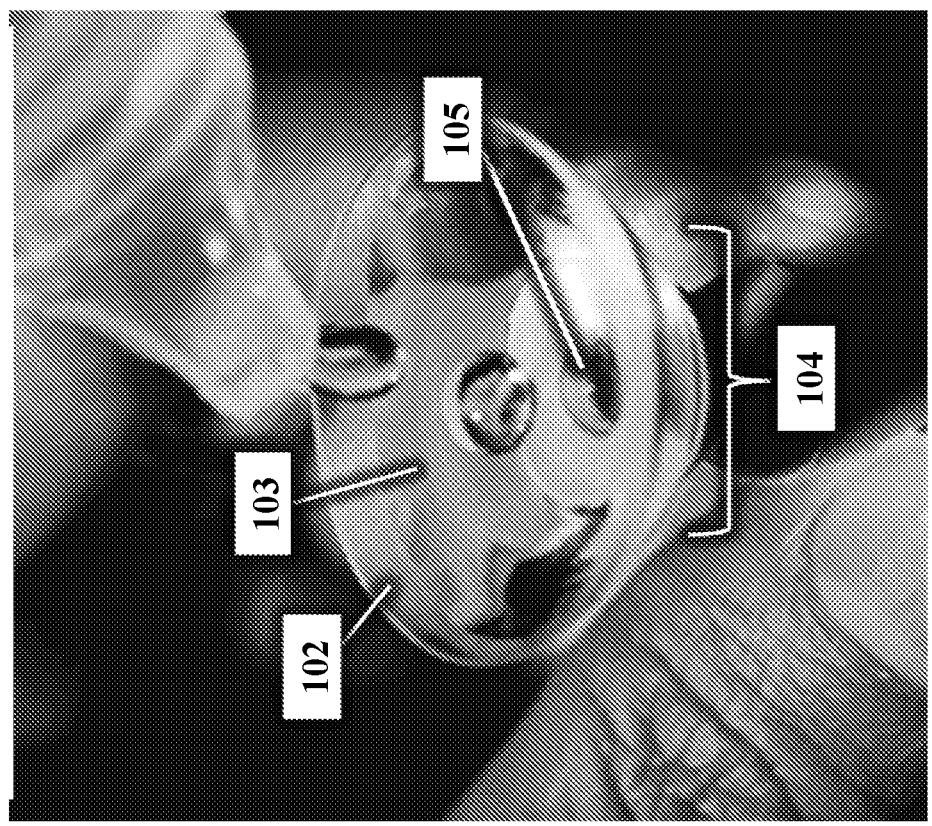
FIG. 2 is a photograph of a scleral lens prosthetic device being filled with sterile saline solution according to some embodiments of the present inventions.

Embodiments of the present inventions include new methods, systems, and devices for translating the theoretical visual benefits of correcting higher-order aberrations into practical improvements in optical and visual performance, by recognizing and quantifying the actual optical and physiological information underlying aberrations. These methods and systems allow a clinician to design and fabricate patient-customized scleral lens prosthetic devices. More specifically, embodiments of the present inventions allow a clinician to improve or at least maintain vision and/or treat or at least reduce symptoms associated with higher-order aberrations.

First, new methods and systems for designing scleral lens prosthetic devices customized to improve or at least maintain vision and/or treat or at least reduce symptoms associated with higher-order aberrations are disclosed. Second, new methods and systems for fabricating scleral lens prosthetic devices customized to improve or at least maintain vision and/or treat or at least reduce symptoms associated with higher-order aberrations are disclosed. Third, these as well as other methods and systems for evaluating customized scleral lens prosthetic devices using quantitative feedback and determining when a device is fit for patient use are disclosed. Also disclosed are devices customized for improving or at least maintaining vision and/or treating or at least reducing symptoms associated with higher-order aberrations.

Although described with respect to higher-order aberrations, the same or similar methods and systems could apply to improving or at least maintaining vision and/or treating or at least reducing symptoms associated with other aberrations. Ocular aberrations, especially higher-order aberrations, may result from progressive disorders like keratoconus, wherein the cornea may become increasingly thin to the point of rupture; hence symptoms, once present, are progressively less likely to improve on their own.

While soft contact lenses with irregular surface profiles were hoped to have some potential in correcting higher-order aberrations and improving vision, the reduction in higher-order aberrations and improvement in vision were relatively small when the lenses were used in keratoconus eyes. Soft contact lenses are less successful at masking anterior corneal aberrations because the tear reservoir between the posterior lens surface and the anterior corneal surface is too minimal to achieve refractive index matching.

In addition, soft contact lenses are limited by lens flexure because the lenses conform to the cornea as well as the effects of variable and dynamic lens movement on the eye. Even accounting for variability of lens position on the eye between blinks (e.g., stabilizing horizontal and vertical decentration and rotational orientation), significant residual higher-order aberrations induced by internal optics, especially the posterior corneal surface, still degraded retinal image quality.

Meanwhile, both rigid gas permeable corneal lenses and scleral lens prosthetic devices achieve some correction of aberrations by masking irregularities on the anterior corneal surface with an artificial tear reservoir between the posterior lens surface and the anterior corneal surface to achieve refractive index matching. However, since these devices correct only for anterior corneal aberration, significant posterior corneal aberrations remain uncompensated. In addition, aberrations such as coma and astigmatism induced by rotation also significantly degrade retinal image quality.

A difference between rigid gas permeable corneal lenses and scleral lens prosthetic devices is the dynamic movement of these corrective devices on an eye. The corneal rigid gas permeable lenses, which are about 8-12 mm in diameter and cover only 75-80% of the cornea, slide with each blink because of this only partial corneal coverage, thus losing the stability of correction.

On the other hand, scleral lens prosthetic devices have diameters ranging from 12-25 mm depending on type, whether corneo-scleral or full scleral. Because scleral lens prosthetic devices rest on the sclera over a large portion of the eye, they have excellent positional stability on the eye between blinks. High patient satisfaction, in terms of wearing comfort, has been observed with these scleral lens prosthetic devices in the management of corneal abnormality, despite the difficulty of wearing devices with such large diameters. For example, patients with corneal ectasia may be relieved of the pressure exerted on their corneas by contact lenses because scleral lens prosthetic devices vault to form a tear reservoir above an irregularly shaped cornea. A scleral lens prosthetic device may be designed with channels on its posterior surface to improve the flow of tears into the reservoir to maintain corneal health. Unlike soft contact lenses, scleral lens prosthetic devices also maintain their physical attributes when placed on the eye (instead of conforming to the ocular surface) and at least partially compensate for anterior corneal irregularities by the aforementioned tear film masking and resultant refractive index matching. Recognition of its positional stability, in concert with these additional benefits, has led to use of a scleral lens prosthetic device as an initial test device and as a base for a final device.

Although the embodiments of the present inventions are described with respect to scleral lens prosthetic devices, the same methods and systems may be used with other devices.

Figure 1:
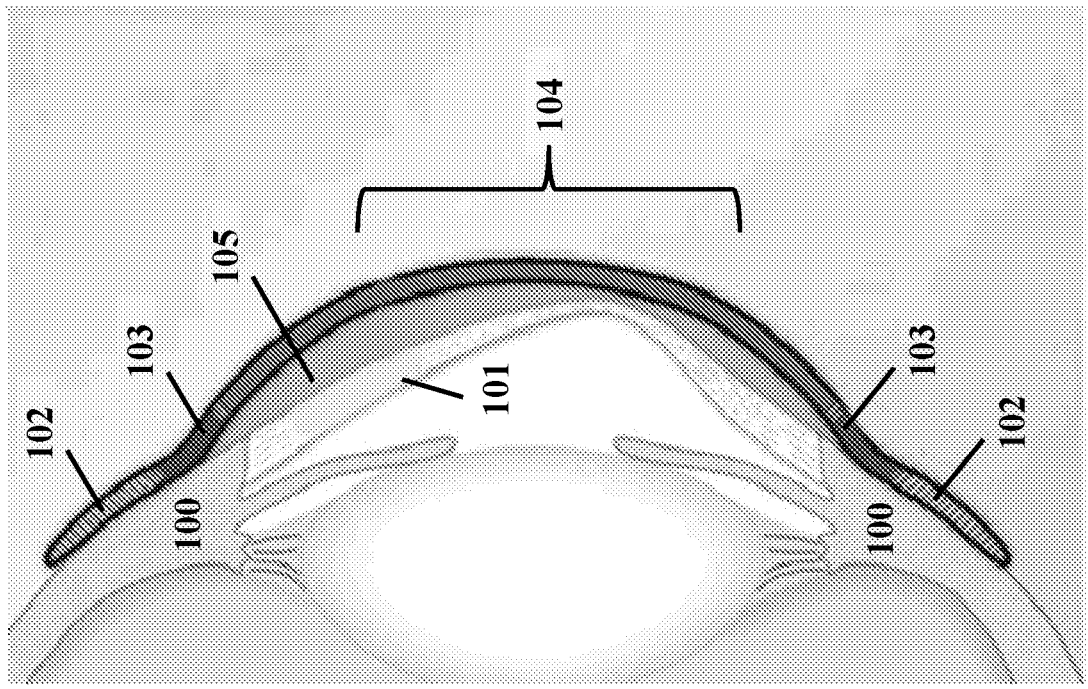
FIG. 1 is a schematic diagram of a scleral lens prosthetic device fitted to an eye with higher-order aberrations according to some embodiments of the present inventions.

FIG. 1 is a schematic diagram of a cross-section of a scleral lens prosthetic device fitted to an eye with higher-order aberrations caused by, for example, keratoconus according to some embodiments of the present inventions. The sclera 100 is the white outer surface of the eye, visible around the cornea 101, which is the clear front surface. In FIG. 1, the cornea 101 is irregularly-shaped. Higher-order aberrations have changed the side profile of the cornea 101 from a normal gradual curve to a conical shape with a thin high point. These corneal irregularities may refract, reflect, and/or absorb light as it reaches the cornea 101, thus affecting the eye's ability to receive and focus the light and resulting in distorted retinal images and reduced visual acuity.

In the schematic diagram in FIG. 1, a peripheral haptic zone 102 of the scleral lens prosthetic device rests entirely on the sclera 100. The curve of the scleral lens prosthetic device includes at least one steeper transitional zone 103 then vaults over the cornea 101 to form a central optic zone 104, creating a tear reservoir 105 between the scleral lens prosthetic device and the corneal surface. The tear reservoir 105 may be filled with sterile saline solution and/or other beneficial agents prior to application to the eye according to some embodiments of the present inventions.

FIG. 2 is a photograph of a scleral lens prosthetic device, being filled with sterile saline solution according to some embodiments of the present inventions. The scleral lens prosthetic device in FIG. 2 is an FDA-approved, rigid gas-permeable scleral lens prosthetic device designed with an expanded oxygenated tear reservoir and marketed as BostonSight PROSE™ (Prosthetic Replacement of the Ocular Surface Ecosystem) (Boston Foundation for Sight, Needham, Mass.). The scleral lens prosthetic device restores function to the entire ocular surface system by creating a transparent, smooth optical surface over the irregular, damaged, and/or diseased cornea and by protecting the corneal surface from adverse effects of the environment and eyelid abnormalities.

Figure 3:
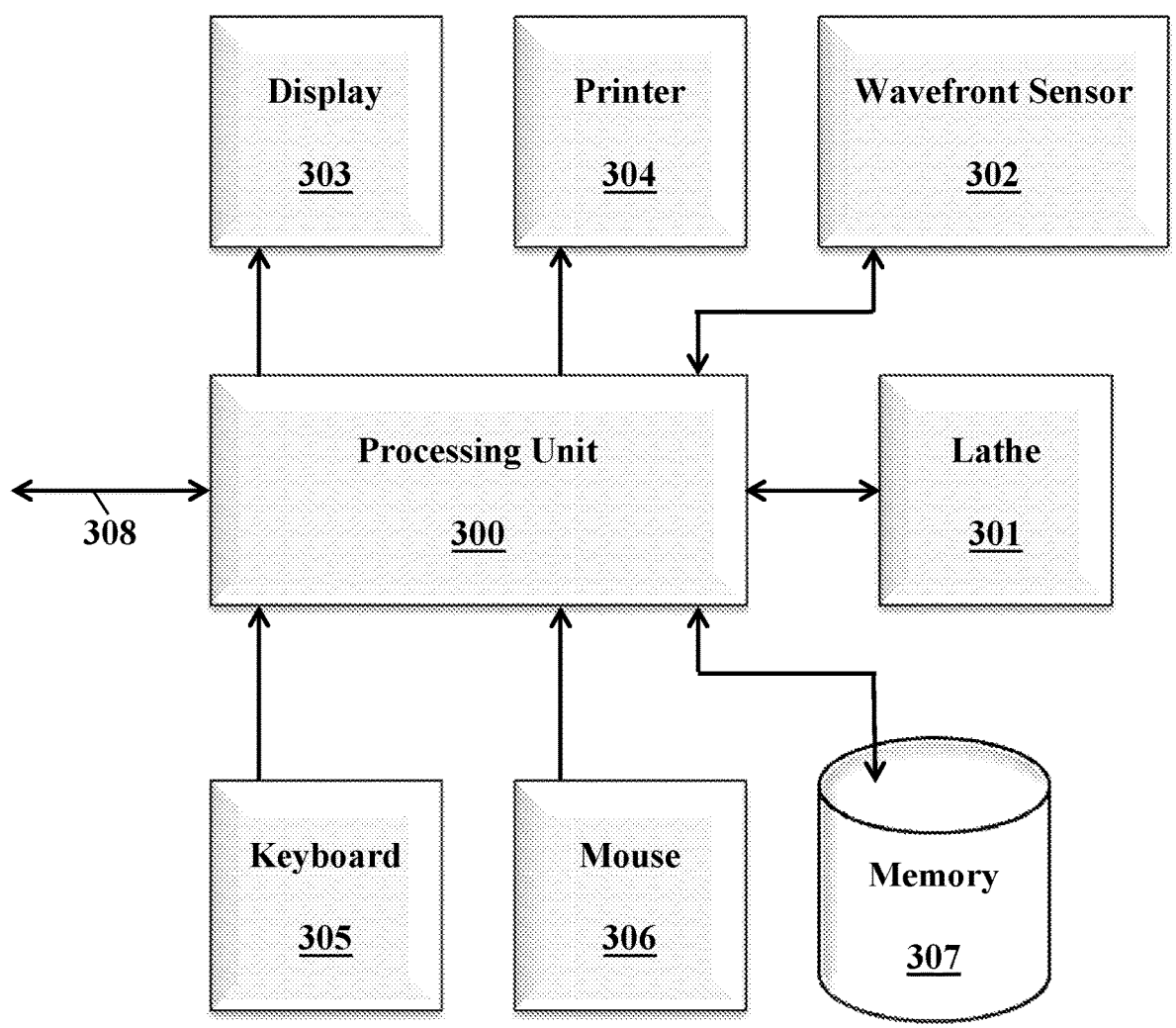
FIG. 3 is a block diagram of a manufacturing system according to some embodiments of the present inventions.

Referring to FIG. 3, in a typical operating environment, a system for manufacturing a scleral lens prosthetic device in accordance with the illustrated embodiment of the invention has a central processing unit 300, appropriately programmed, to operate a computer-controlled lathe 301. The processing unit 300 is also appropriately programmed to operate a computer-controlled wavefront sensor 302. The processing unit 300 has typical peripheral elements such as a display 303, a printer 304, a keyboard 305, a mouse 306, and a memory unit 307. The processing unit 300 can also receive data according to one aspect of the invention from other, potentially remote, sites over one or more wired or wireless communication network connections 308.

In practice, embodiments of the present inventions may be implemented in various forms of hardware, software, firmware, or a combination thereof. In some embodiments, modules are implemented in software as application programs that are then executed by user equipment. The user equipment may include desktop computers, laptop computers, netbooks, smartphones, and other forms of audio/visual equipment that can communicate with a network, a wavefront sensor (e.g., an aberrometer or Shack-Hartman wavefront sensor), and/or a fabrication unit (e.g., a computer-controlled lathe). In certain embodiments of the present inventions, separate central processing units are used for various processes. For example, three central processing units can be used: one for collecting data from a wavefront sensor, one for generating designs for a scleral lens prosthetic device based on input from the wavefront sensor as well as other sources, and one for controlling the lathe during device fabrication.

A central processing unit executes processes performed by the user equipment. The user equipment can be configured with one or more processors that process instructions and run software that may be stored in memory. In some embodiments, the software needed for implementing a process or a database includes a high level procedural or an object-orientated language such as C, C++, C#, Java, or Perl. Applicable processors can include any microprocessor (single or multiple core), system on chip (SoC), microcontroller, digital signal processor (DSP), graphics processing unit (GPU), combined hardware and software logic, or any other integrated circuit capable of processing instructions. Suitable operating systems can include MAC OS, Linux, Unix, MS-DOS, Windows, or any other operating system capable of executing the processes described below.

Certain embodiments of the present inventions may include one or more suitable memory units, such as a non-transitory computer readable medium, flash memory, a magnetic disk drive, an optical drive, a programmable read-only memory, and/or a read-only memory. The one or more memory devices may also store the instructions for the below processes, which are executed by a central processing unit.

Certain embodiments of the present inventions may include one or more user interfaces to provide input and/or output mechanisms to communicate with a user. The one or more user interfaces can be implemented in hardware or software. The one or more user interfaces can be used to receive both data and control information from a network (using, e.g., a modem, wireless transceiver, or wired network connection) as well as local sources. Suitable input/output devices may include, but are not limited to, a screen, a touch screen, a monitor, a printer, a modem, a transceiver, a keyboard, a microphone, a speaker, a pen device, a trackball, a touch pad, and a mouse. The one or more user interfaces can operate under a number of different protocols. In some embodiments the one or more user interfaces are implemented through software, and in other embodiments, the one or more user interfaces are implemented in hardware to send and receive signals via transceiver in a variety of mediums, such as optical, copper, and wireless.

Figure 4:
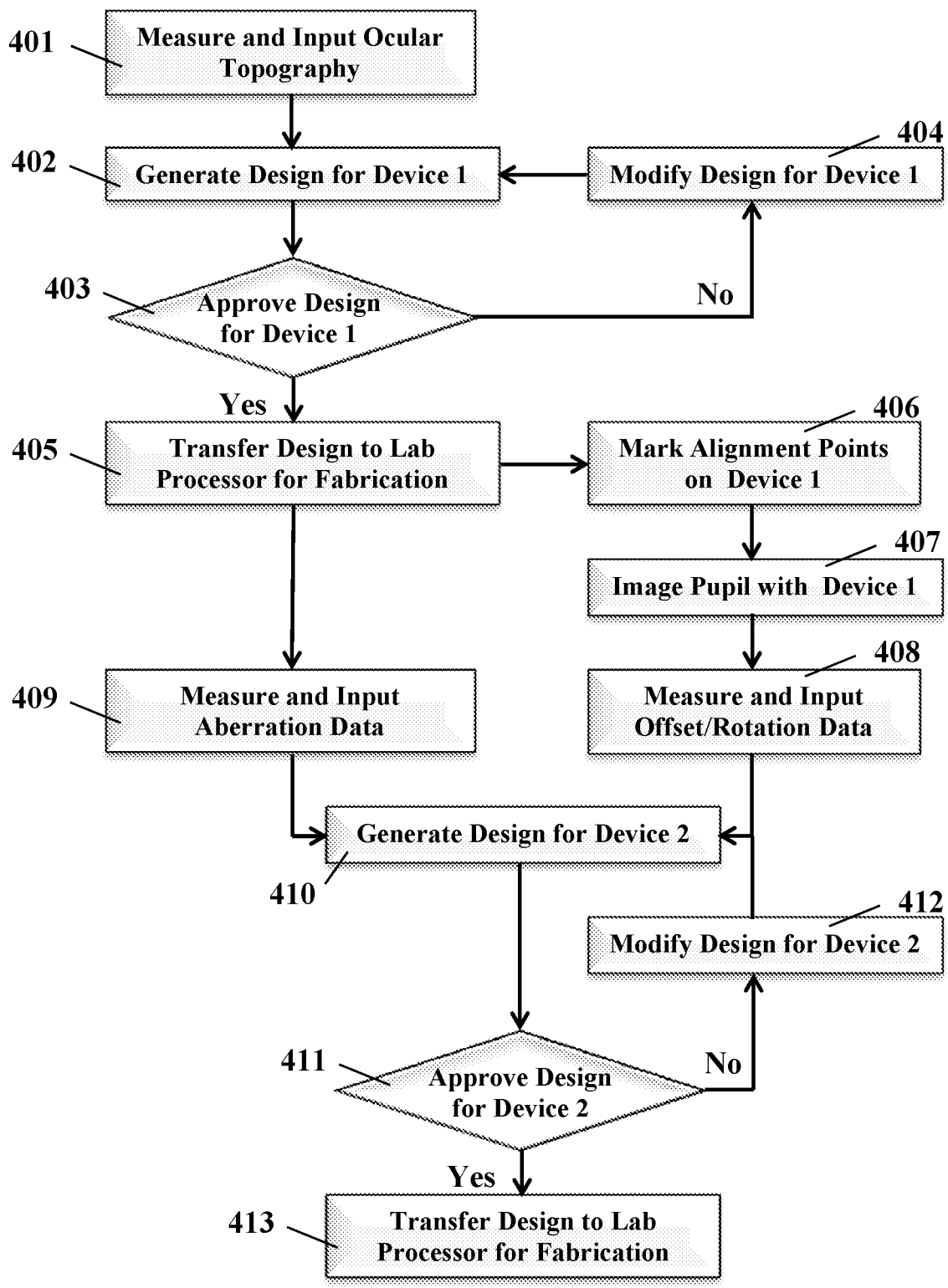
FIG. 4 is a flow chart of steps in manufacturing a device according to some embodiments of the present inventions.

In a typical operation of the apparatus of FIG. 3, and referring to FIG. 4, a clinician can measure, or estimate, the corneoscleral surface topography and input that topography to the computer system at 401. Other data useful to define a scleral lens prosthetic device may also be input, such as a clinically desirable axial edge clearance, or other clinical or optical constraints. The computer system then generates an approximation to the corneoscleral surface topography at 402, using, for example, a spline curve fitting approximation, in a manner to be described in more detail below. The result of the curve approximation, representing a design for an initial test device, can be displayed to the clinician, preferably in an interactive session. If the clinician finds the resulting curve fit acceptable, then the device design is approved at 403 and can be transferred to the lab processor to be fabricated at 405. If the curve fit is not acceptable, for example because it fails to provide proper edge clearance, or makes substantially excess contact with the cornea, or for a number of other clinical reasons, the clinician in an interactive session using the keyboard, mouse, and display can provide for an alteration of the computer generated curve and thereafter generate a new curve to fit the now refined and changed input data to improve the approximation of the refined corneoscleral topography. Such modifications are made at 404, and the steps of input, approximation, display, and refinement, if necessary, can be repeated. Once the design has been approved at 403, the data is transferred to the lab processor to be fabricated at 405. Thus, the scleral lens prosthetic device, when appropriately fitted, provides a stable platform into which custom wavefront-guided refractive correction can be embedded.

During or after fabrication, precise alignment points can be lathe-cut around the edge of the scleral lens prosthetic device to determine its movement on the eye at 406. A surgical marking pen may be used to color the alignment marks with dark (e.g., black) ink under a microscope, to aid their visibility in pupil images. The clinician can then image the pupil while the patient wears the scleral lens prosthetic device at 407. From the pupil images, the clinician can measure or estimate any decentration and/or rotation of the device in relation to the pupil and input the measurements to the computer system at 408.

Before, after, or simultaneous with the above pupil imaging 407, the clinician can measure or estimate optical aberrations while the patient wears the scleral lens prosthetic device using, for example, an aberrometer and/or a Shack-Hartmann wavefront sensor and input the measurements to the computer system at 409.

The computer system then generates a wavefront-guided surface profile for a customized scleral lens prosthetic device with the design of the initial test device as a baseline and compensating for any decentration, rotation, and/or aberrations present in the optic zone at 410. The wavefront-guided surface profile can be displayed to the clinician, preferably in an interactive session. If the clinician finds the profile acceptable, then the device design is approved at 411 and can be transferred to the lab processor to be fabricated at 413. If the compensation is not acceptable, for example because it fails to provide proper centration or for a number of other clinical reasons, the clinician in an interactive session using the keyboard, mouse, and display can provide for an alteration of the wavefront-guided surface profile and thereafter generate a new profile to fit the now refined and changed input data to improve the device design. Such modifications are made at 412, and the steps of input, compensation, display, and refinement, if necessary, can be repeated. Once the design has been approved at 411, the data is transferred to the lab processor and the lens to be fabricated at 413.

According to some embodiments of the present inventions, a clinician uses a computer-aided design and/or computer-aided manufacturing (CAD/CAM)-type application to design and fabricate scleral lens prosthetic devices. The clinician may use the CAD/CAM-type application to customize the optic zone and/or the transitional zone of a scleral lens prosthetic device to neutralize refractive error and address anatomic anomalies of the corneoscleral topography. In some embodiments, each contour of the device may be specified separately based on clinical criteria for "fit," for example, by mathematically describing each contour with a spline function.

As shown in the schematic diagram in FIG. 5A, a scleral lens prosthetic device may be designed and modeled using spline functions according to some embodiments of the present inventions. For example, vault control spline 500 allows the clinician to specify the vault of a scleral lens prosthetic device independent of the base curve of the optic zone 104. This design flexibility and the very high degree of customization of a scleral lens prosthetic device according to some embodiments of the present inventions ensures ability to achieve good fit and high level of prosthetic function. FIG. 5B is a display screen shot of a scleral lens prosthetic device modeled using a CAD/CAM-type application according to some embodiments of the present inventions. This application incorporates by reference the entire contents of U.S. Pat. No. 5,452,031, issued Sep. 19, 1995, and assigned to Boston Foundation for Sight (Needham, Mass.).

Two design features of a scleral lens prosthetic device are that it does not touch the cornea and that there is minimal movement of the weight-bearing haptic zone on the sclera. The former is accomplished by the large diameter and vault over the cornea. The latter is accomplished by precise alignment of the haptic zone with the sclera.

As above, the clinician may use the CAD/CAM-type application to customize the posterior surface of the haptic zone of a scleral lens prosthetic device so that it aligns with the scleral surface. The process of aligning the haptic zone to the sclera of a particular eye is resource-intensive, requiring trial and/or production of numerous devices per eye, combined with training the patient in device application and removal, with visits spread out over time based on proximity to the site of manufacturing and on patient and clinician scheduling preferences.

Different approaches to fitting a scleral lens prosthetic device may be utilized according to some embodiments of the present inventions. In some embodiments using a diagnostic approach, an initial trial device is selected based on a subjective clinical assessment of the diameter and vault likely to be required, and subsequent modification and refinement of contours are then carried out in an iterative process in which incremental changes are sequentially evaluated on the eye. In some embodiments using an empiric approach, which is used typically for rigid gas permeable corneal contact lens fitting, a parameter of an initial trial device is selected empirically to be steeper than K, with K referring to keratometry reading or a simulated value taken from videokeratography. In some embodiments, the fit of a trial device is based on clinical assessment of numerous parameters over increasing time intervals. An apparently inadequate device is removed immediately after application and assessment. A satisfactory device is reassessed after 1 hour, 3 hours, and then 6 hours, at which time specific parameters are modified by selection of another device from an inventory of trial devices or by design and manufacture of a more appropriate device.

According to some embodiments of the present inventions, images may be used as part of or a basis for a diagnostic, empiric, automated, or combination approach to patient-customized design and fitting of scleral lens prosthetic devices.

Figure 6B:
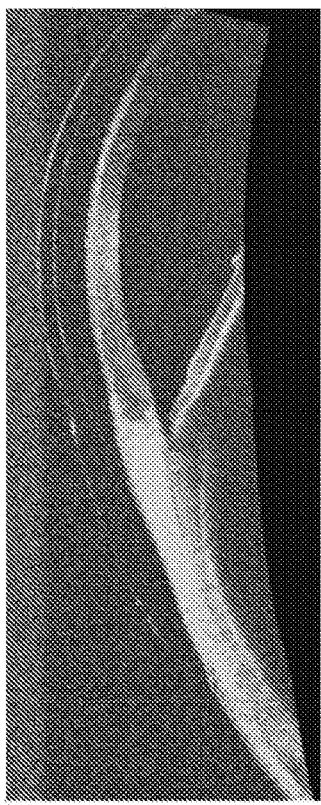
FIGS. 6A-6B are optical coherence tomography images of an eye before and after de-warping according to some embodiments of the present inventions.
Figure 6A:

For example, optical coherence tomography (OCT) is a non-contact imaging technology that provides detailed (e.g., micrometer-resolution) cross-sectional images of internal structures in biological tissues. FIGS. 6A-6B are OCT images of an eye obtained with a prototype time domain 1310 nm wavelength anterior segment OCT scanner (Optovue, Inc., Freemont, Calif.). FIG. 6A is an image before the application of OCT image processing software. FIG. 6B is the same image after de-warping with OCT image processing software.

Figure 7:
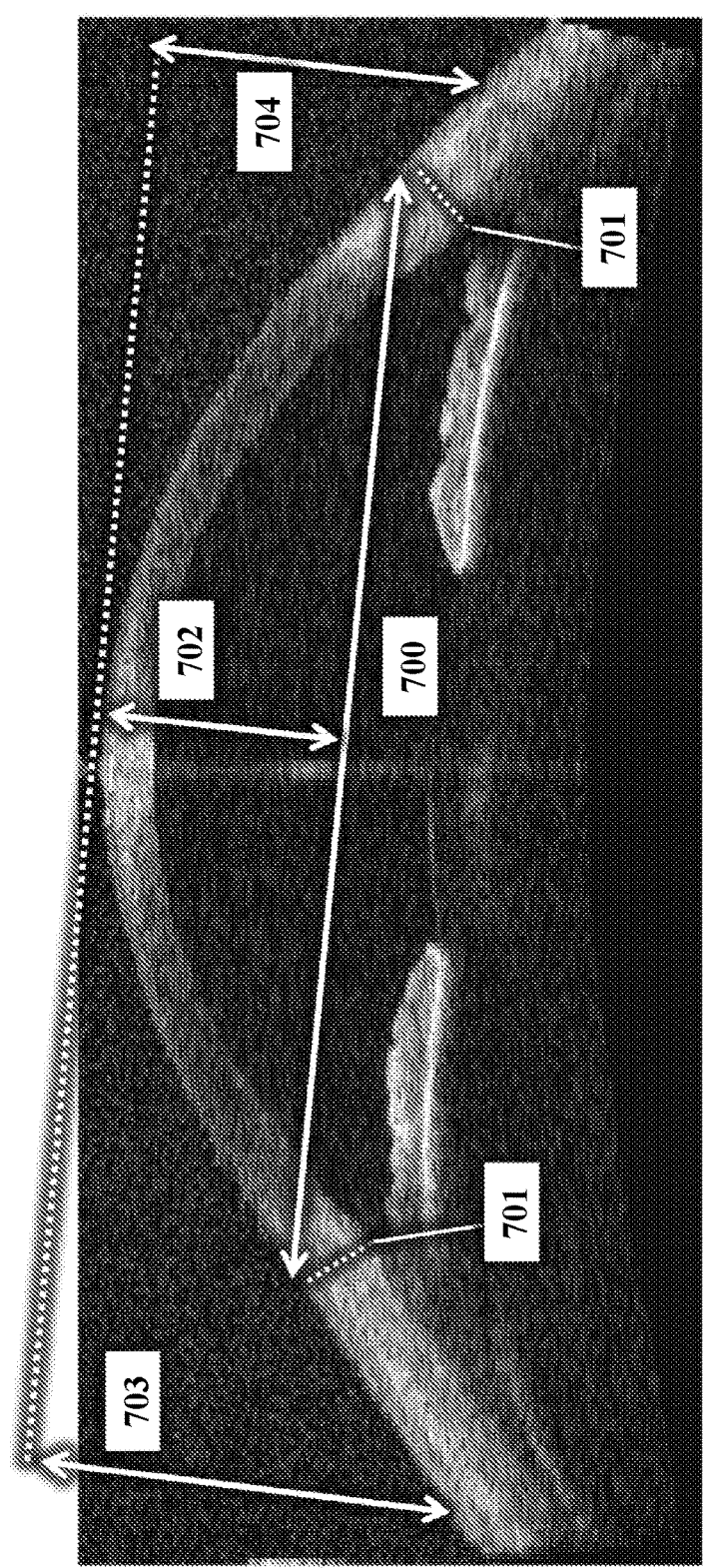
FIG. 7 is an optical coherence tomography image of a normal cornea according to some embodiments of the present inventions.
Figure 8A:
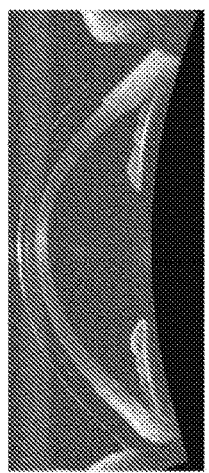
FIG. 8A is a vertical optical coherence tomography image of an anterior globe contour with a lid artifact according to some embodiments of the present inventions.
Figure 8B:
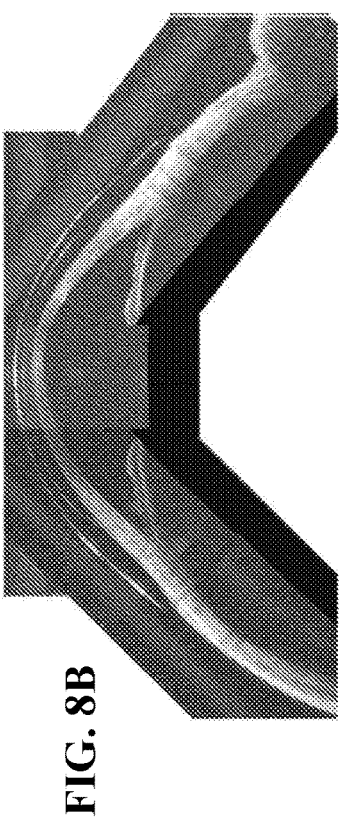
FIG. 8B is a montage of optical coherence tomography images obtained in deviated gaze to create an image of the entire anterior globe contour absent lid artifact according to some embodiments of the present inventions.

High-resolution OCT of the anterior segment of the eye can provide data on the shape of the sclera which is not available via keratometry or videokeratography. FIG. 7 is an OCT image of a normal cornea for which an elevation profile was generated using OCT image processing software. The image dimension in FIG. 7 is 18 mm and consists of 256 axial scans acquired in 0.128 second. By analyzing an OCT image like FIG. 7, a clinician may obtain measurements of corneal diameter 700 (i.e., the distance between the scleral spurs 701 in the OCT image derived from scans along the horizontal and vertical meridians), corneal sagittal height 702 (i.e., the perpendicular distance from corneal apex to the chord of corneal diameter 700), scleral sagittal height 704 (i.e., the perpendicular distance from a chord (e.g., 17 mm in length), parallel to the corneal apex, to the sclera), and scleral toricity (i.e., the difference in average scleral sagittal height between the horizontal (0° and 90°) and vertical (90° and 270°) meridians). Meanwhile, FIG. 8A is a vertical OCT scan with a lid artifact. Using a montage of OCT images obtained in deviated gaze, a clinician may create an image, as shown in FIG. 8B, of the entire anterior globe contour absent the lid artifact.

Thus, according to some embodiments of the present inventions, high-resolution anterior segment OCT may be used to provide profiles and indices useful for specifying appropriate contours for a scleral lens prosthetic device, including device corneal height (i.e., the perpendicular distance from the on-eye device posterior surface to the chord of corneal diameter 700), device sagittal height (i.e., the perpendicular distance from a chord (e.g., 17 mm in length) to the device posterior surface), and device toricity (i.e., the difference in average device sagittal height between the horizontal (0° and 90°) and vertical (90° and 270°) meridians).

Figure 9B:
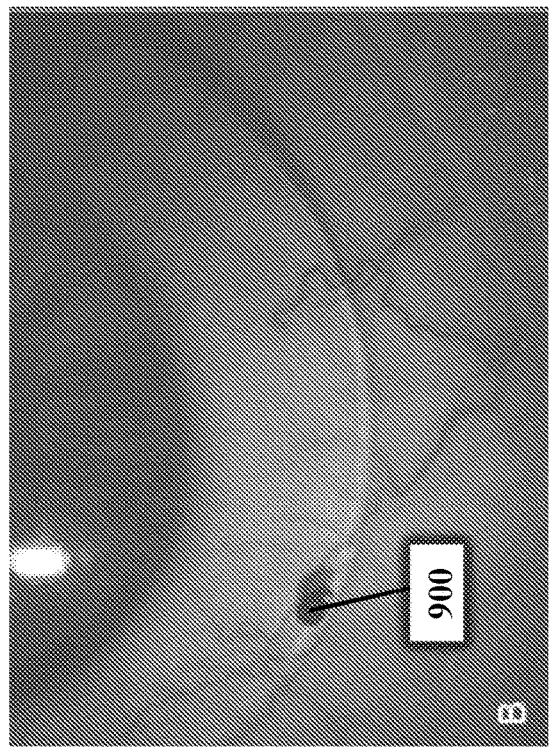
FIGS. 9A-9B are slit lamp photographs showing device orientation markings used to define a sampling axis of the device profile to test for correlation with scleral toricity according to some embodiments of the present inventions.
Figure 9A:
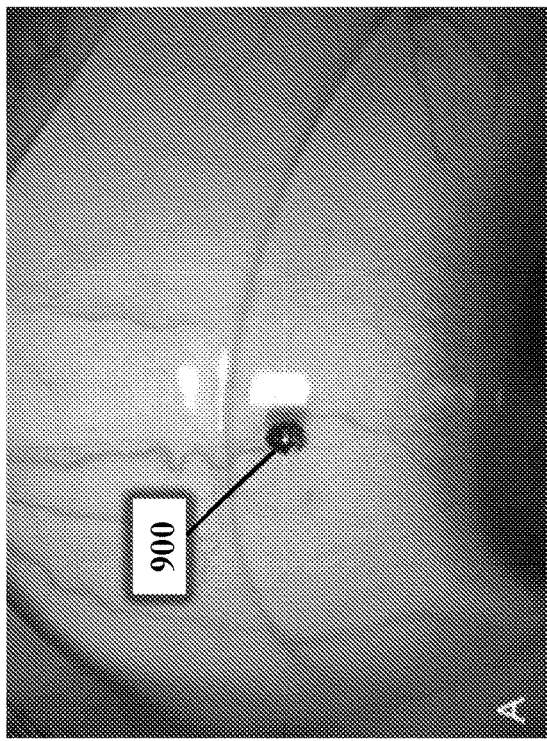

Slit lamp imaging is another useful technology for documenting the orientation and clinical features of fit for a scleral lens prosthetic device. For example, FIGS. 9A-9B are slit lamp photographs showing device orientation markings 900 used to define a sampling axis of the device profile to test for correlation with scleral toricity according to some embodiments of the present inventions. Rotation of the scleral lens prosthetic device was achieved by adjusting the device sagittal heights. The eye pictured in FIG. 9A has 0 degrees of rotation, while the eye pictured in FIG. 9B has 30 degrees of rotation.

Because the profiles of the cornea and/or sclera are irregular, some patients may need a scleral lens prosthetic device with varying profiles or contours, including in the haptic zone. To accommodate this individual variability in the device, the haptic zone may be divided into two or more sections, with the contours of each section independently specified. The number of different contours in the haptic zone of a scleral lens prosthetic device determines the haptic type. For example, FIGS. 10A-10D are diagrammatic representations of various haptic types according to some embodiments of the present inventions. In these representations, the haptic zone has been divided into quadrants. FIG. 10A represents a radially (and rotationally) symmetric or spherical haptic type with a continuous contour 1001. FIG. 10B represents a toric haptic type with two different contours 1001 and 1002. FIG. 10C represents a radially asymmetric haptic type with three different contours 1001, 1002, and 1003. FIG. 10D represents a radially asymmetric haptic type with four different contours 1001, 1002, 1003, and 1004.

Figure 11:
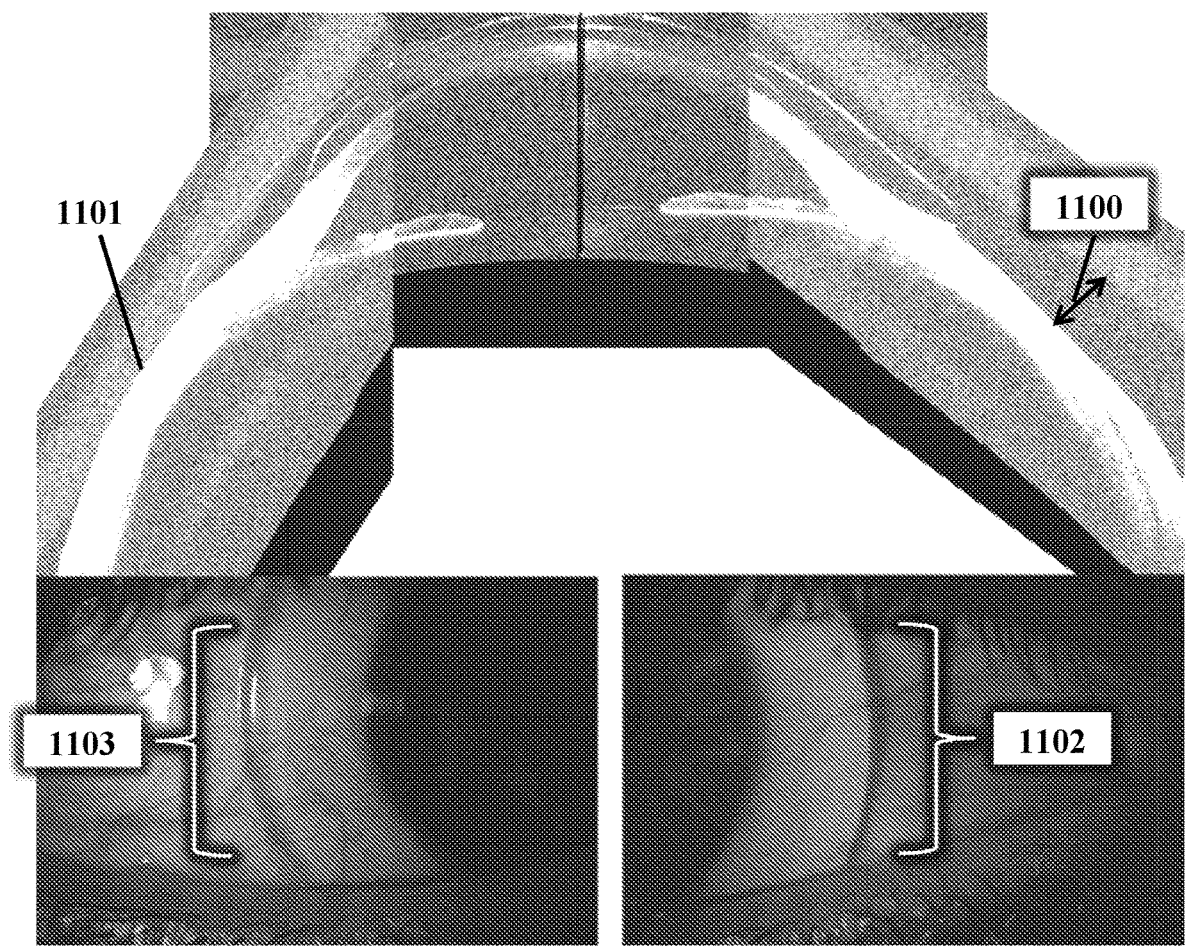
FIG. 11 is a montage of optical coherence tomography images and slit lamp photographs illustrating a satisfactory fit and an unsatisfactory edge lift of a scleral lens prosthetic device according to some embodiments of the present inventions.

The haptic type of a scleral lens prosthetic device may be adjusted to accommodate for unsatisfactory features of fit such as haptic compression, edge lift, and/or failure to accurately adjust for device rotation on the eye. FIG. 11 is a horizontal montage of OCT images and slit lamp photographs showing an unsatisfactory edge lift 1100 on one side of a scleral lens prosthetic device but a satisfactory fit 1101 on the opposite side of the device according to some embodiments of the present inventions. The unsatisfactory edge lift 1100 is marked by shadow 1102 just peripheral to the nasal edge of the haptic in the corresponding slit lamp photograph, while the satisfactory fit 1101 is observed as neither lifted nor compressed alignment 1103 of the haptic with sclera in the corresponding slit lamp photograph opposite.

According to some embodiments of the present inventions, one or more measurements, images, or other data on corneal, limbal, and scleral contours are entered into the CAD/CAM-type application, either streamlining or bypassing part or all of the diagnostic, iterative process by which device and scleral contours are matched in the customization process.

Figure 12:
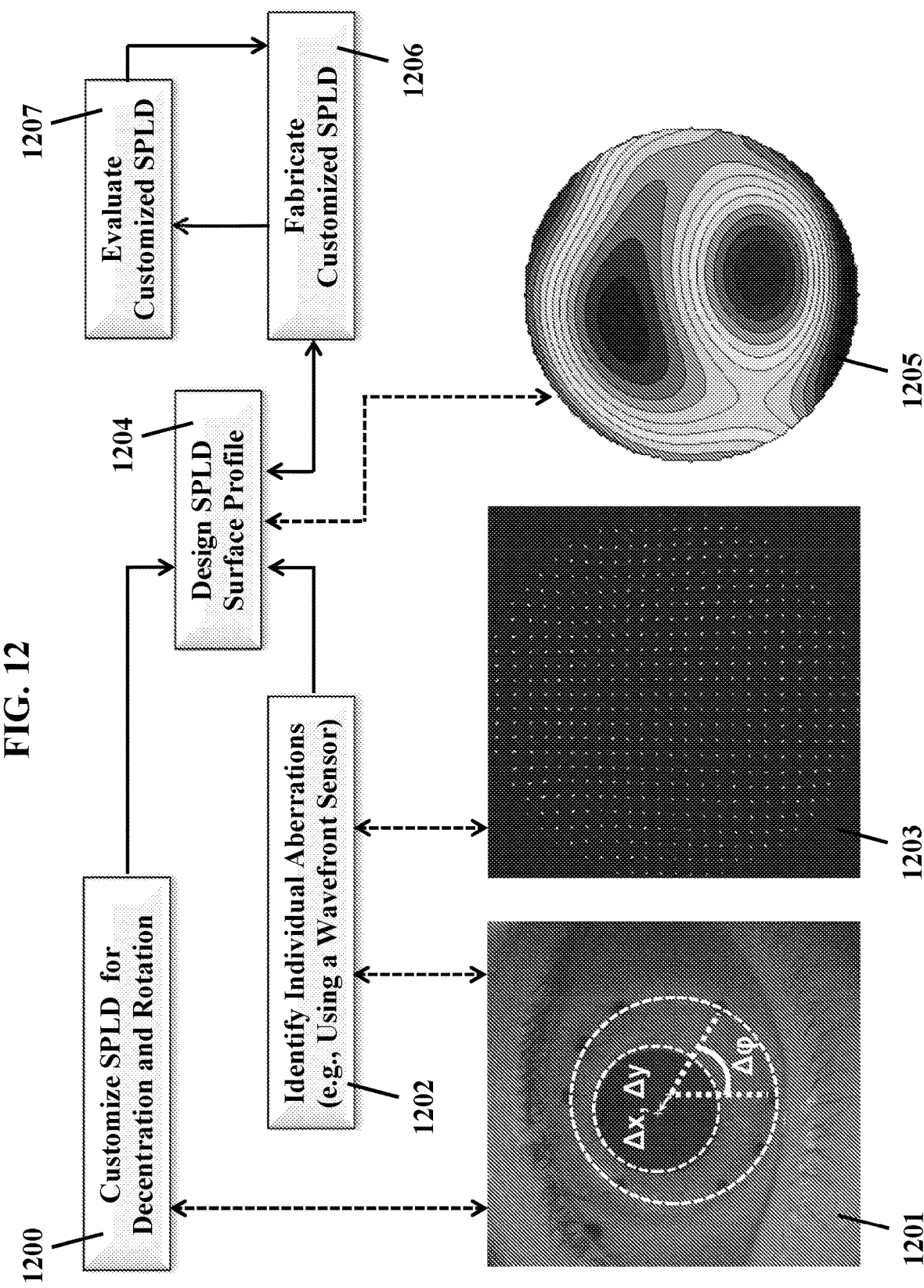
FIG. 12 is a procedural diagram for designing, manufacturing, and evaluating a customized wavefront-guided scleral lens prosthetic device according to some embodiments of the present inventions.

FIG. 12 is a procedural diagram for designing, fabricating, and evaluating a customized wavefront-guided scleral lens prosthetic device according to some embodiments of the present inventions. In step 1200, a clinician fits a scleral lens prosthetic device customized to account for potential decentration and rotation, as described above in more detail, based on one or more measurements of a patient's eye.

Briefly, the patient is fitted first with a scleral lens prosthetic device with spherical optics. This initial test device features a central optic zone with a customized peripheral haptic surface that aligns precisely with the scleral surface. Spline functions are used to create seamless transition zones, allowing control of vault above the cornea independent of lens base curve. According to some embodiments of the present inventions, the device has varying amounts of back surface toricity that vary independently between, for example, four quadrants. Back surface toricity provides the alignment of the haptic zone to the eye's scleral shape, but it does not provide any optical toricity.

In this manner, the fit of the scleral lens prosthetic device is customized to each eye in order to minimize its dynamic movement. Precise alignment points are lathe-cut around the edge of the scleral lens prosthetic device to determine its movement on the eye. A surgical marking pen is used to color the alignment marks with dark ink under a microscope, to aid their visibility in pupil images 1201. Thus, the scleral lens prosthetic device, when appropriately fitted, provides a stable platform into which custom wavefront-guided refractive correction can be embedded.

In step 1202, the clinician identifies aberrations in the eye using, for example, an aberrometer or a Shack-Hartmann wavefront sensor to obtain a spot pattern 1203. According to some embodiments of the present inventions, the pupil of the patient's eye is dilated using, for example, tropicamide (e.g., 0.5% or 1%) ophthalmic solution, so that one or more wavefront aberration measurements can be obtained over the larger area. Aberrations of the eye are measured while the eye is wearing the customized scleral lens prosthetic device using, for example, an aberrometer and/or a Shack-Hartmann wavefront sensor. In some embodiments, the aberrometer and/or wavefront sensor has simultaneous pupil imaging capability to capture pupil images 1201.

Figure 13A:
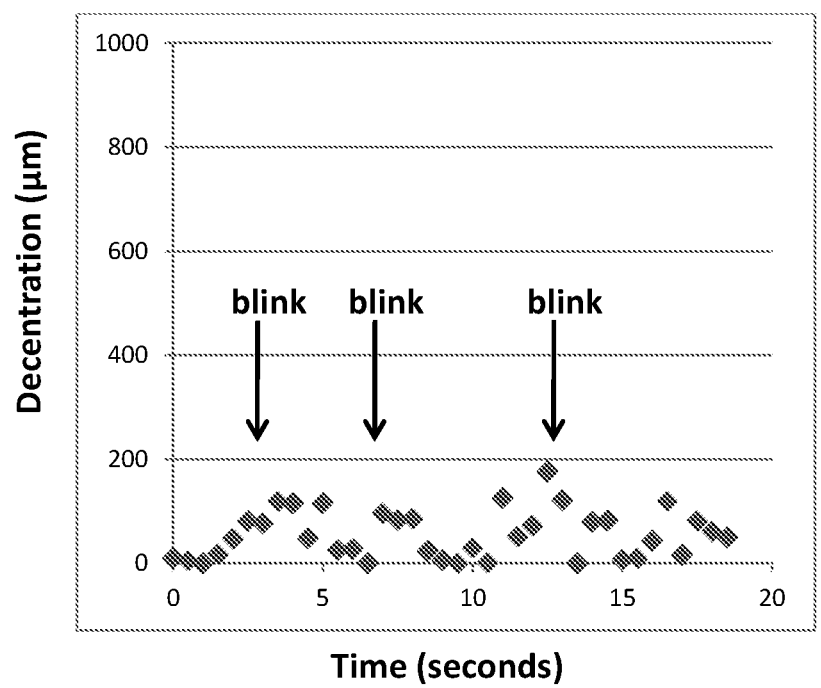
FIGS. 13A-13B are plots of the magnitude of vector decentration and rotation of a conventional scleral lens on an eye with keratoconus over a time period including three natural blinks according to some embodiments of the present inventions.
Figure 13B:
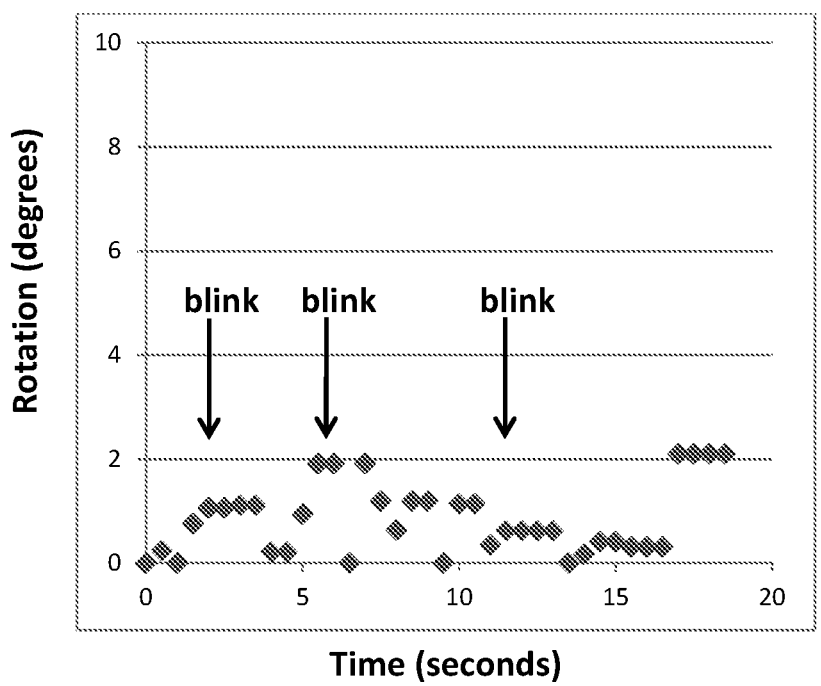

For example, in a study of patients with advanced keratoconus, six patients (eleven eyes) were fit with spherical scleral lens prosthetic devices according to some embodiments of the present inventions. A Shack-Hartmann wavefront sensor was used to measure aberrations in the patients wearing the devices after dilating their pupils. The position (i.e., horizontal and vertical decentration with respect to the pupil center and rotational orientation) of the devices were also measured and taken into account in the design of the final wavefront-guided scleral lens prosthetic devices. From the designed x and y decentration and rotation, the customized wavefront-guided scleral lens prosthetic devices deviated by 63.4 µm, 136.9 µm and 6.9 degrees, respectively on average, between the eyes. In addition, the wavefront-guided scleral lens prosthetic devices exhibited good stability on the eye between blinks. FIGS. 13A-13B show the magnitude of vector decentration (A) and rotation (B) with time over three natural blinks, when wavefront-guided scleral lens prosthetic device was placed on one advanced keratoconus eye. The average decentration and rotation over time was 67.3±54.5 µm and 0.94±58 degrees respectively.

In alternative embodiments, the clinician may identify aberrations in an eye using a wavefront sensor without having the eye wear an initial trial scleral lens prosthetic device. The clinician may even predict the position (i.e., horizontal and vertical decentration with respect to the pupil center and rotational orientation) of a final device relative to the eye's pupil without fabricating an initial trial scleral lens prosthetic device (e.g., based on the corneoscleral surface topography). In such embodiments, any aberrations in the eye and/or the predicted position of a customized scleral lens prosthetic device inform the fabrication of the device.

In step 1204, the clinician combines one or more measurements from steps 1200 and 1202 to design a wavefront-guided surface profile 1205 for the customized scleral lens prosthetic device using, for example, a CAD/CAM-type program (e.g., custom-built software in C++ programming language).

A wavefront is a surface over which an optical disturbance has a constant phase. Rays and wavefronts are two mutually complementary approaches to light propagation. Wavefronts are always normal (perpendicular) to the rays. For light to converge to a perfect point, the emerging wavefront must be a perfect sphere centered on the image point. The distance in microns between the actual wavefront and the ideal wavefront is the wavefront aberration, which is the standard method of showing the aberrations of the eye. Therefore, aberrations of the eye are the difference between two surfaces: the ideal wavefront and the actual wavefront.

Figure 14B:
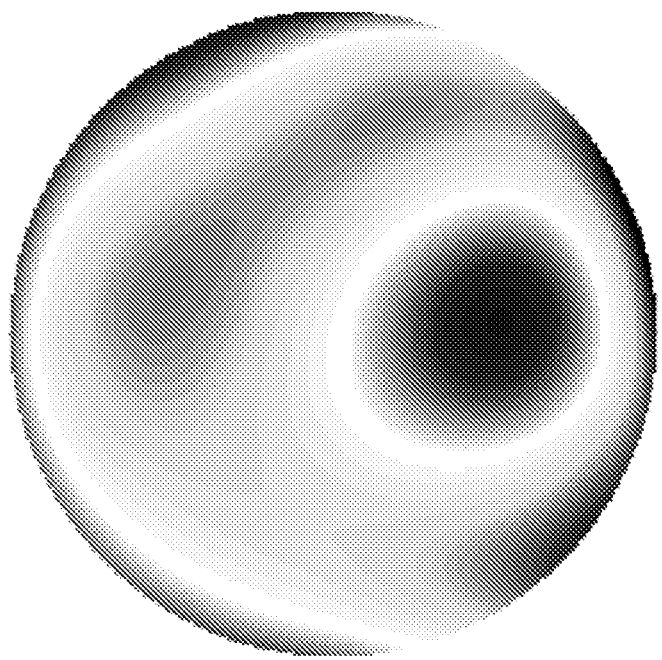
FIGS. 14A-14B are higher-order wavefront maps of an eye with advanced keratoconus measured using a Shack-Hartmann wavefront sensor for designing and fabricating a customized scleral lens prosthetic device according to some embodiments of the present inventions.
Figure 14A:
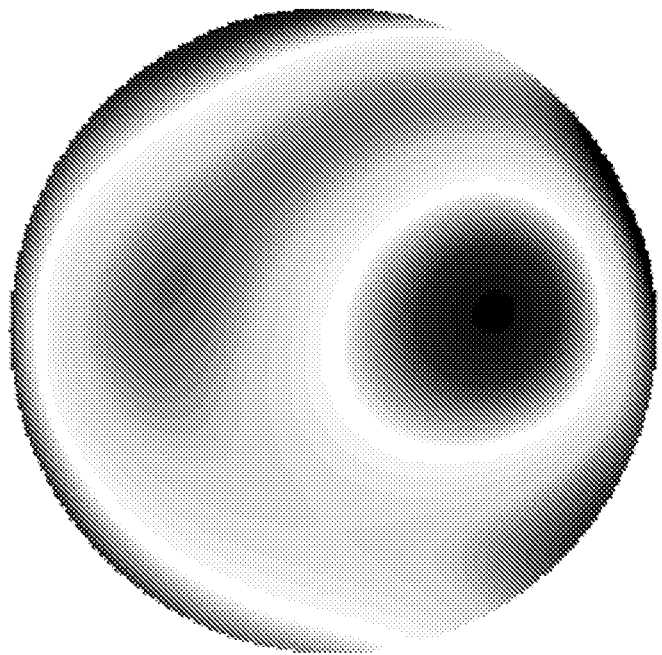

For example, in the study of six patients (eleven eyes) with advanced keratoconus, higher-order wavefront maps were collected using a Shack-Hartmann wavefront sensor according to some embodiments of the present inventions. For one of the eyes, FIG. 14A shows the higher-order wavefront map for the designed customized wavefront-guided scleral lens prosthetic device, and FIG. 14B shows the higher-order wavefront map for the fabricated customized scleral lens prosthetic devices.

Quantitative comparisons between different eyes and conditions are usually made using root mean square (RMS). In order to measure RMS, for each type of aberration the difference between the aberration and mean value is squared and averaged across the pupil area. Different kinds of aberrations may have equal RMS across the pupil but have different effects on vision; therefore, RMS error is unrelated to visual performance. In the study, the higher-order RMS for the designed scleral lens prosthetic devices was 2.30 µm over a 7.5 mm pupil. The error in fabrication, defined as the higher-order RMS difference between the designed and fabricated customized scleral lens prosthetic devices, was 0.2 µm.

The most common method of classifying the shapes of aberration maps is to consider each map as the sum of fundamental shapes or basis functions. One popular set of basis functions are the Zernike polynomials, which are used to describe aberrations of the cornea or lens from an ideal spherical shape, which result in refraction errors. Each aberration may be positive or negative in value and induces predictable alterations in the image quality. Zernike polynomials are usually expressed in terms of polar coordinates $(\rho,\theta)$, where $\rho$ is the radial coordinate and $\theta$ is the angle. For each polynomial the mean value of the aberration across the pupil is zero, and the value of the coefficient gives the RMS error for the particular aberration for the particular pupil diameter.

In each Zernike polynomial $Z_n^m$, the subscript n is the order of aberration, and the superscript m is the angular frequency. The Zernike modes include the following:

TABLE 1

| Zernike Term | Common Name |
| --- | --- |
| $Z_0^0$ | Piston |
| $Z_1^1, Z_1^{-1}$ | Tilt or Prism |
| $Z_2^0$ | Defocus |
| $Z_2^2, Z_2^{-2}$ | Astigmatism |
| $Z_4^2, Z_4^{-2}$ | Secondary Astigmatism |
| $Z_4^0$ | Spherical Aberration |
| $Z_3^1, Z_3^{-1}$ | Coma |
| $Z_3^3, Z_3^{-3}$ | Trefoil |
| $Z_4^4, Z_4^{-4}$ | Quadrafoil |

Figure 15A:
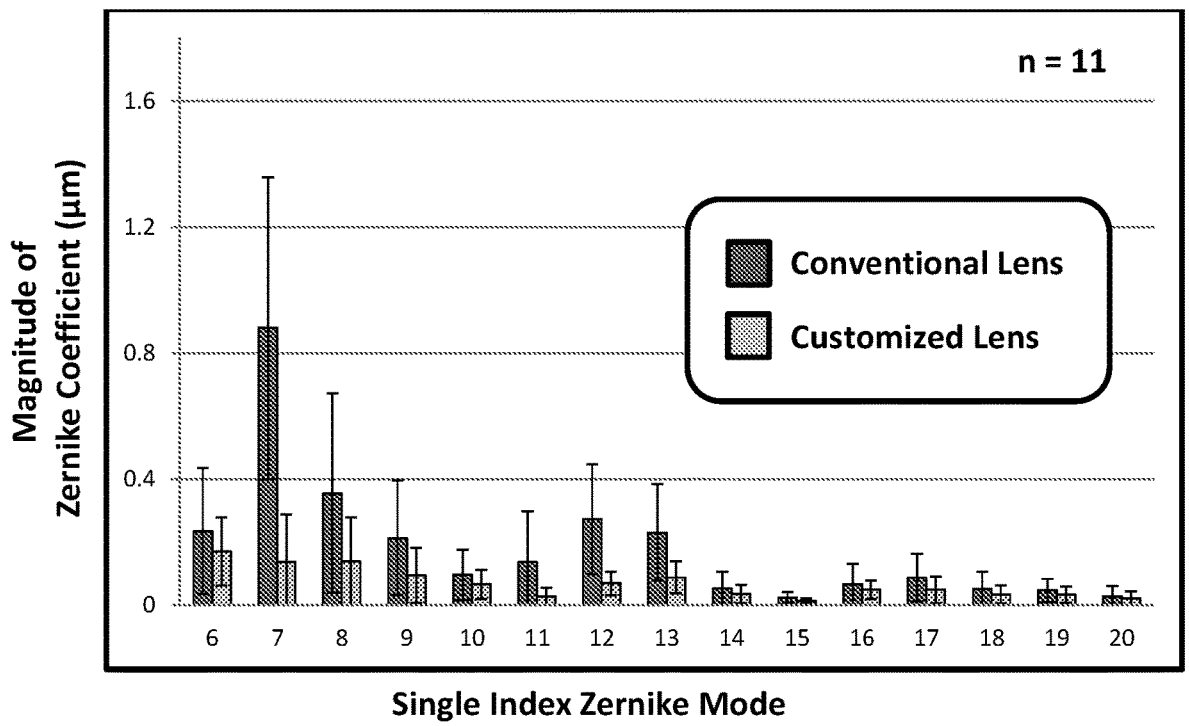
FIG. 15A is a plot of the average magnitude of the Zernike coefficients, according to the single value modes suggested in the ANSI Z80.28-2004 standard, measured with a conventional scleral lens and with a customized scleral lens prosthetic device in eleven eyes with severe keratoconus, according to some embodiments of the present inventions.
Figure 15B:
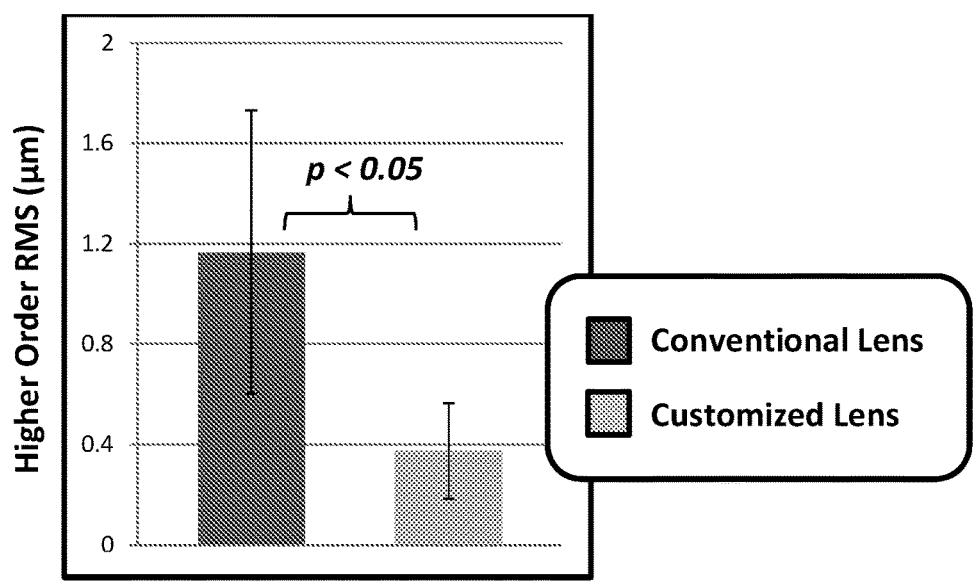
FIG. 15B is a plot of the average higher-order root-mean-square measured with a conventional scleral lens and with a customized scleral lens prosthetic device in eleven eyes with severe keratoconus according to some embodiments of the present inventions.

FIG. 15A shows the wavefront aberration in terms of the magnitude of the Zernike polynomial coefficients, according to the single value modes suggested in the ANSI 280.28-2004 standard, which is incorporated herein by reference, as measured with conventional scleral lenses and customized wavefront-guided scleral lens prosthetic devices over a 6 mm pupil in the study of the eleven11 keratoconus eyes. Also shown in FIG. 15B is the higher-order RMS of the aberrations in both cases. Mean±standard deviation of higher-order RMS of the eyes with the conventional lens was 1.17±0.57 µm for a 6 mm pupil. The most dominant higher-order aberration was positive vertical coma that accounted for 79% of the total higher-order aberrations. Vertical coma and secondary astigmatism (Zernike single mode numbers 7 and 13 respectively) were the only two aberrations which were consistently positive across all patients with the conventional scleral lenses. Most of the higher-order aberrations were effectively corrected by the customized wavefront-guided scleral lens prosthetic devices, and higher-order RMS was reduced 3.1 times on average to 0.37±0.19 µm for the same 6 mm pupil. Thus, a level of aberration similar to that observed in a normal population was achieved.

According to some embodiments of the present inventions, the Zernike coefficients and/or the Shack-Hartmann spot pattern are entered in the CAD/CAM-type program. The program computes a wavefront profile designed to be fabricated on the optic zone of the customized wavefront-guided scleral lens prosthetic device in order to compensate for the measured aberrations.

According to some embodiments of the present inventions, a CAD/CAM-type program (e.g., software in MAT-LAB® (The Mathworks, Inc., Natick, Mass.)) geometrically determines the offset and rotation of the patient's pupil relative to known landmarks on the initial trial scleral lens prosthetic device designed in step 1200 from photographs 1201 taken during the step 1202. The static horizontal decentration ($\Delta x$), vertical decentration ($\Delta y$), and rotation ($\Delta \varphi$) of the lens with respect to the pupil center is quantified from one or more pupil images 1201. In alternative embodiments, a user determines the offset and rotation relative to the pupil and enters the measurements into the program. The program computes a profile of the customized wavefront-guided scleral lens prosthetic device designed to account for decentration and rotation of the device.

In step 1206, a new customized wavefront-guided scleral lens prosthetic device is fabricated. According to some embodiments of the present inventions, a sub-micron precision, computerized lathe (e.g., a computer numerical controlled (CNC) lathe such as Precitech Nanoform 250, AME-TEK, Precitech, Inc., Keene, N.H.) is used to diamond-turn the device, including the irregular profile on the anterior optic surface of the device. The design of a lathe may vary, but a CNC lathe typically has a turret to hold and/or index the tool holders, which allows multiple cutting operations to be performed, each with a different cutting tool, in easy succession, with no need for the operator to perform setup tasks in between. Slides allow the turret to move in multiple axes simultaneously. The spindle is configured to hold the device (using, e.g., chucks or faceplates). According to some embodiments of the present inventions, the lathe can be controlled electronically via a computer menu style interface.

The design data, programmed by the CAD/CAM-type program or manually by a programmer, may be translated into machining data (e.g., cutting tool paths and coordinates) to direct the lathe. The resulting machining data file (e.g., a C++ file) is uploaded to the lathe processor, and in some embodiments of the present inventions, the fabrication may be simulated and displayed before or simultaneously to fabrication.

According to some embodiments of the present inventions, the CAD/CAM-type program provides real-time control of the fabrication tool (e.g., a lathe) during the cutting of the device. Calculations are performed in real-time to direct rotation (e.g., spindle speed) of the lathe spindle, the vertical/horizontal movement of the cutting tool, and/or the vertical/horizontal movement of the device. In other embodiments of the present inventions, the machining data from the CAD/CAM-type program is pre-calculated and applied with minimal or no modifications during fabrication.

According to some embodiments, a diamond-turned scleral lens prosthetic device starts out as a cylindrical disk held in the jaws of the lathe. The lathe is equipped with an industrial-grade diamond as the cutting tool. The lathe may turn at 6000 RPM as the cutting tool removes the desired amount of material from the posterior surface of the device in a series of one or more passes of decreasing depth. The posterior surface of the device may be polished with some fine abrasive paste, oil, and/or a small polyester cotton ball turned at high speeds. In order to hold the delicate device in reverse manner, wax may be used as an adhesive. The anterior surface of the device thus may be cut and polished by the same process.

In alternative embodiments, a scleral lens prosthetic device may be fabricated methods including spin-casting (i.e., adding molten material to a revolving mold at high speed so that the device is shaped at least in part by centrifugal forces) and injection molding.

In step 1207, the clinician evaluates the new customized wavefront-guided scleral lens prosthetic device and may re-fabricate (repeating step 1206) and even re-design (repeating step 1204) based on appropriate correction factors until a satisfactory fit, optical performance, and/or visual performance is achieved.

The customized wavefront-guided scleral lens prosthetic device is evaluated using optical metrology (e.g., an aberrometer or Shack-Hartmann wavefront sensor) to determine the precision of its fabrication. According to some embodiments, optical metrology is performed with a Shack-Hartmann wavefront sensor specifically designed to measure the optical aberrations of contact and scleral lenses in vitro, whether in their dry or hydrated state. Aberration measurements are performed for the customized wavefront-guided scleral lens prosthetic device and compared with its corresponding design parameters.

On-eye performance is evaluated, according to some embodiments, by another Shack-Hartmann wavefront sensor by measuring optical aberrations with the initial trial customized scleral lens prosthetic device and the customized wavefront-guided scleral lens prosthetic device in situ. The pupil of the eye is optically conjugated to the Shack-Hartmann microlens array (with, e.g., 0.67× de-magnification, spacing of 150 µm, and a focal length of 3.76 mm). The spot pattern formed by the microlens array is imaged on a charge coupled device camera (with, e.g., 6.45 µm pixel size). Wavefront aberrations are calculated from this spot array pattern and decomposed into coefficients of Zernike polynomials up to the 6th order. The eye's pupil is imaged using a camera focused at the pupil plane under infra-red light emitting diode illumination, simultaneously with the wavefront measurement.

Visual acuity is a measure of the spatial resolution of this optical system and its ability to resolve detail. Visual acuity may be tested by having a patient identify standardized test symbols of progressively smaller size on an eye chart from a distance predetermined to approximate infinity in the way the lens attempts to focus (e.g., 20 feet). Lenses of varying powers and a pinhole may be used to correct for refractive errors. The test symbols or optotypes are specially shaped letters, numbers, or geometric shapes (e.g., alphabet characters in a standard Snellen chart, broken rings in a Landolt C chart, or rotated "E"s in a tumbling "E" chart), usually printed in black against a white background for maximum contrast. In the Snellen chart the smallest letters are composed of lines separated by a visual angle of one arcminute (i.e., the lines are spaced only about 1.75 mm apart). Larger letters have lines separated by correspondingly larger visual angles. Visual acuity is measured by finding the smallest symbol a patient can identify and calculating the distance at which it has a visual angle of 5 arcminutes.

In the expression "20/40 vision," "20" is the distance in feet between the patient and the chart and "40" means the patient can read the chart as well as a person with normal vision could read the same chart from 40 feet away. Vision of 20/20 is considered nominal performance, 20/40 vision is considered half as good as nominal performance, and 20/10 vision is considered twice as good as nominal performance. Visual acuity may be expressed as a fraction (e.g., "20/20"), a decimal number representing the reciprocal value of the size of the gap of the smallest symbol identified (e.g., "1.00"), or a logarithm of the minimum angle of resolution as measured on a Log MAR chart (e.g., "0.00"). These visual acuity scales are illustrated in the following chart:

TABLE 2

| Snellen Fraction | Decimal | LogMAR |
|---|---|---|
| 20/200 | 0.10 | 1.00 |
| 20/160 | 0.125 | 0.90 |
| 20/125 | 0.16 | 0.80 |
| 20/100 | 0.20 | 0.70 |
| 20/80 | 0.25 | 0.60 |
| 20/63 | 0.32 | 0.50 |
| 20/50 | 0.40 | 0.40 |
| 20/40 | 0.50 | 0.30 |
| 20/32 | 0.63 | 0.20 |
| 20/25 | 0.80 | 0.10 |
| 20/20 | 1.00 | 0.00 |
| 20/16 | 1.25 | −0.10 |
| 20/12.5 | 1.60 | −0.20 |
| 20/10 | 2.00 | −0.30 |

According to some embodiments of the present inventions, visual performance is evaluated monocularly under natural mesopic pupil condition by measuring best corrected high contrast tumbling "E" visual acuity and contrast sensitivity using a calibrated cathode ray tube display. The display is placed some fixed distance (e.g., 10 feet) from the patient in a dark room. The untested eye is occluded. The tumbling "E" test uses the four-alternate forced-choice method where the illiterate letter "E" is presented to the observer in one of four orientations (0°, 90°, 180°, or 270°, and the observer's task is to respond to the orientation of the letter by pressing the appropriate button. Visual acuity is determined as the line thickness of the letter for which at least a determined percentage (e.g., 60%) of the observer's responses are correct.

Contrast sensitivity is measured similarly using the two-alternate forced-choice method where the observer's task is to distinguish the orientation of 2-D Gabor functions, shown either vertically or horizontally. A 2-D Gabor function is a sinusoidal luminance distribution overlaid with a Gaussian envelope and is routinely used in several psychophysical experiments. Contrast threshold at, for example, 4 c/deg, 8 c/deg, and 12 c/deg (where the size of the visual field on the retina is 3 deg). is determined by the contrast at the respective spatial frequency for which at least a determined percentage (e.g., 75%) of the observer's responses are correct.

Figure 16:
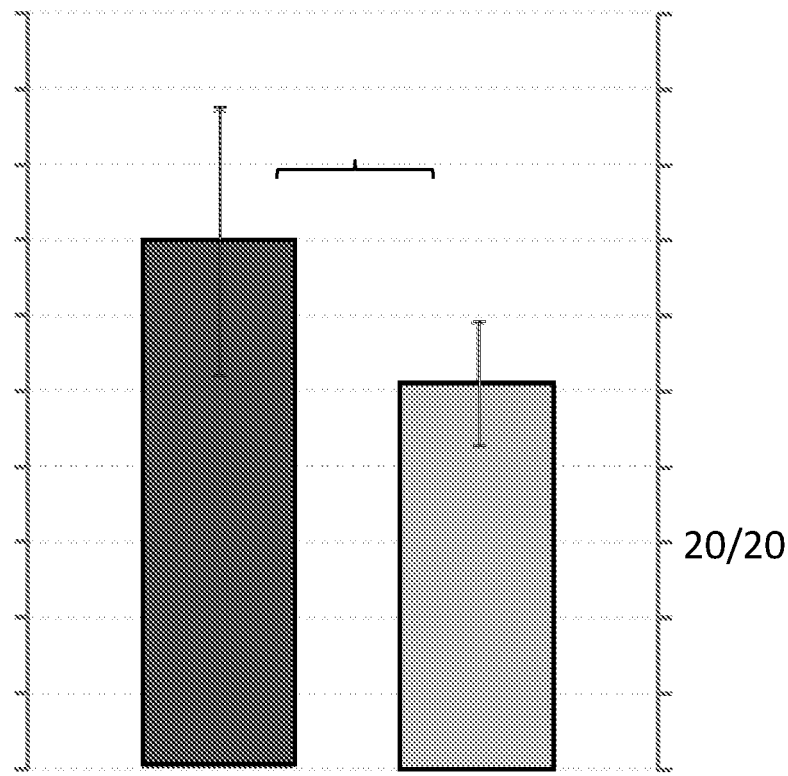
FIG. 16 is a plot of the average visual acuity measured with a conventional scleral lens and with a customized scleral lens prosthetic device in eleven eyes with severe keratoconus, as viewed through the natural mesopic pupil, according to some embodiments of the present inventions.

FIG. 16 shows the average visual acuity measured with a conventional scleral lens and with a customized wavefront-guided scleral lens prosthetic device, as viewed through the natural mesopic pupil, in the study of eleven eyes with severe keratoconus according to some embodiments of the present inventions. The optical correction resulted in significant improvement of 1.9 lines on average in visual acuity.

Figure 17:
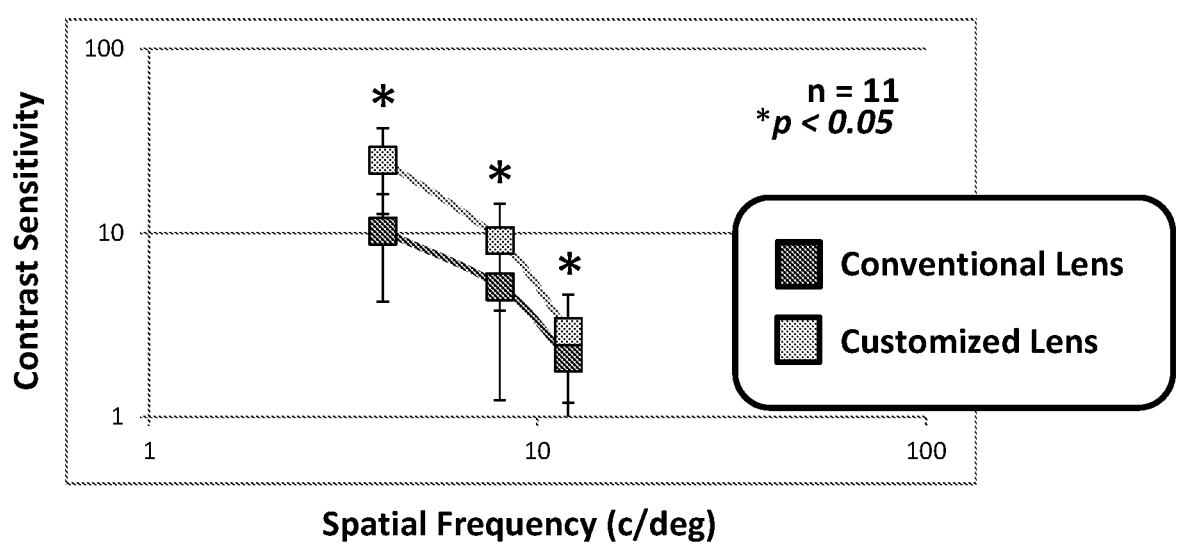
FIG. 17 is a plot of the average contrast sensitivity over spatial frequencies of 4, 8, and 12 cycles per degree measured with a conventional scleral lens and with a customized scleral lens prosthetic device in eleven eyes with severe keratoconus, as viewed through the natural mesopic pupil, according to some embodiments of the present inventions.

FIG. 17 shows the average contrast sensitivity over spatial frequencies of 4 c/deg, 8 c/deg, and 12 c/deg measured with a conventional scleral lens and with a customized wavefront-guided scleral lens prosthetic device, as viewed through the natural mesopic pupil, in the study of eleven eyes with severe keratoconus according to some embodiments of the present inventions. Contrast sensitivity was also significantly improved by a factor of 2.4, 1.8, and 1.4 on average for 4 c/deg, 8 c/deg, and 12 c/deg respectively. All patients reported a remarkable improvement in subjective image quality.

FIGS. 18A-18B present the case of the advanced keratoconus eye whose optical quality with the customized wavefront-guided scleral lens was the best among the eleven eyes in the study. In this eye, the higher-order root-mean-square of 1.67 µm with the conventional lens was reduced to a value of 0.22 µm with the customized lens. FIG. 18A is a wavefront map of the eye measured with a conventional scleral lens, and FIG. 18B is a wavefront map of the eye measured with a customized wavefront-guided scleral lens prosthetic device, using a Shack-Hartmann wavefront sensor according to some embodiments of the present inventions.

With the customized correction, the high contrast visual acuity was improved by 2 lines, as shown in FIG. 19, while the contrast sensitivity improved by a factor 5.9, 4.8, and 3.8 for 4 c/deg, 8 c/deg, and 12 c/deg respectively, over the conventional correction. However, even with the incredible optical correction with the customized lens, the Snellen visual acuity was still 20/28.4, significantly worse than normal eyes. The Snellen visual acuity in 4 normal eyes with comparable native higher-order RMS of 0.25±0.04 µm over the same 6 mm pupil was also measured and is shown in FIG. 7B. With similar level of optical quality, these normal eyes obtained Snellen visual acuity of 10.7±0.3, close to the approximate upper-bound sampling-limited visual acuity of 20/10.

Customized wavefront-guided scleral lenses thus offer a superior optical correction of highly aberrated eyes to around what is typically observed in normal eyes. However, the visual acuity was still significantly poorer than what is typically observed in the normal population over the same pupil size. For instance, in the case of the patient shown in FIGS. 18A-18B, the residual higher-order RMS was as low as 0.22 µm over a 6 mm pupil, but the Snellen visual acuity was still significantly worse than normal eyes at 20/28.4. For the same level of higher-order RMS in normal eyes, visual acuity better than 20/15 can be expected. Inexplicable by optical factors, this discrepancy in visual performance might be attributed to post-receptoral neural factors. In particular, long-term visual experience with poor retinal image quality in keratoconus eyes may restrict the visual benefit achievable immediately after the customized correction. For example, as a consequence of chronic exposure to blur in keratoconus eyes, there might be a loss in sensitivity to fine spatial detail as present in a perfect retinal image, thus limiting the visual performance when correcting the ocular optics completely. By the same token, maximum visual performance, as predicted by ocular optics, might also be expected after long term adaptation of the visual system to near-diffraction limited ocular optics.

In summary, customized wavefront-guided scleral lens prosthetic devices provided incredible reduction in higher-order aberrations in severe keratoconus, thus providing them with a normal level of ocular optics. The corrected optics led to a substantial benefit in visual acuity and contrast sensitivity. This establishes the potential of customized wavefront-guided scleral lens prosthetic devices to provide abnormal corneal patients with nearly a normal level of optical and visual quality. In addition, the better subjective preference and corneal health with these devices make them an excellent candidate for habitual wear. The utility of customized wavefront-guided scleral lens prosthetic devices is not only limited to provide normal level of vision for keratoconus and abnormal corneal patients, but can be extended to the design of any optical treatment designated for aberration manipulation.

As will be apparent, the present disclosure can be embodied in forms other than those specifically disclosed above, for example, a fabrication tool other than a lathe (e.g., a spin-casting or molding tool). The particular embodiments described above are, therefore, to be considered as illustrative and not restrictive. The scope of the present inventions is as set forth in the appended claims and equivalents thereof, rather than being limited to the examples contained in the foregoing description.

The invention claimed is:

1. A method for manufacturing a wavefront-guided scleral lens prosthetic device customized for an eye of a patient, comprising:
   obtaining a first scleral lens prosthetic device, having a central optic zone configured to vault over the eye's cornea and a peripheral haptic zone fitted to the topography of the scleral surface of the patient's eye to minimize its dynamic movement;
   marking alignment points on the first scleral lens prosthetic device;
   collecting a first set of one or more measurements through the first scleral lens prosthetic device of at least one of any offset and rotation of the first scleral lens prosthetic device relative to the eye's pupil using the alignment points;
   collecting a second set of one or more measurements of one or more of any aberrations of the eye;
   generating a wavefront-guided profile from the first and second sets of one or more measurements, said profile to be fabricated on a surface of a second scleral lens prosthetic device; and fabricating the second scleral lens prosthetic device with said wavefront-guided profile on a surface of the second scleral lens prosthetic device.

2. The method of claim 1, wherein the one or more of any aberrations include at least one of a secondary astigmatism, a spherical aberration, a coma, a trefoil, a quadrafoil, or a different higher-order aberration caused by at least one of an irregular deformation, a stress line, or a scar on the eye's cornea.

3. The method of claim 1 further comprising manufacturing the second scleral lens prosthetic device on a lathe.

4. The method of claim 1 further comprising:
determining a level of performance of the second scleral lens prosthetic device; and
comparing the level of performance to one or more performance criteria indicative of the level to which a scleral lens prosthetic device at least one of limits fabrication error, performs optically, or performs visually.

5. The method of claim 4, wherein the one or more performance criteria include at least one of optical metrology, visual acuity, or contrast sensitivity.

6. The method of claim 4 further comprising:
obtaining successive scleral lens prosthetic devices if the one or more performance criteria are not met by one or more previous scleral lens prosthetic devices; and
repeating at least one of the steps of (a) collecting a first set of one or more additional measurements of at least one of any offset and rotation of a new first scleral lens prosthetic device relative to the eye's pupil when the new first scleral lens prosthetic device is worn on the eye, (b) collecting a second set of one or more additional measurements of one or more of any aberrations of the eye, (c) generating a new wavefront-guided profile using at least one of the first and second sets of one or more additional measurements, and (d) fabricating a new scleral lens prosthetic device with the new wavefront-guided profile on a surface of the new scleral lens prosthetic device; and
determining a level of performance of each successive new scleral lens prosthetic device until the one or more performance criteria are met.

7. A method for manufacturing a wavefront-guided scleral lens prosthetic device customized for an eye of a patient, comprising:
receiving a first set of one or more measurements through a first scleral lens prosthetic device having a central optic zone configured to vault over the eye's cornea and a peripheral haptic zone fitted to the topography of the scleral surface of the patient's eye to minimize its dynamic movement, wherein said first set of one or more measurements are of at least one of any offset and rotation of the first scleral lens prosthetic device relative to the eye's pupil and are collected using alignment points on the first scleral lens prosthetic device;
receiving a second set of one or more measurements of one or more of any aberrations of the eye;
generating a wavefront-guided profile from the first and second sets of one or more measurements; and
fabricating a second scleral lens prosthetic device with said wavefront-guided profile on a surface of the second scleral lens prosthetic device.

* * * * *